United States Patent
Kaminski et al.

(10) Patent No.: US 12,139,458 B2
(45) Date of Patent: Nov. 12, 2024

(54) (2,5-DIOXOPYRROLIDIN-1-YL)(PHENYL)-ACETAMIDE DERIVATIVES AND THEIR USE IN THE TREATMENT OF NEUROLOGICAL DISEASES

(71) Applicants: UNIWERSYTET JAGIELLONSKI, Cracow (PL); WARSZAWSKI UNIWERSYTET MEDYCZNY, Warsaw (PL)

(72) Inventors: Krzysztof Kaminski, Cracow (PL); Michal Abram, Cracow (PL); Anna Rapacz, Cracow (PL); Szczepan Mogilski, Labowa (PL); Gniewomir Latacz, Wolbrom (PL); Bartlomiej Szulczyk, Warsaw (PL)

(73) Assignees: Uniwersytet Jagiellonski, Cracow (PL); Warszawski Uniwersytet Medyczny, Warsaw (PL)

( * ) Notice: Subject to any disclaimer, the term of this patent is extended or adjusted under 35 U.S.C. 154(b) by 682 days.

(21) Appl. No.: 17/309,956

(22) PCT Filed: Jan. 7, 2020

(86) PCT No.: PCT/PL2020/050001
§ 371 (c)(1),
(2) Date: Jul. 3, 2021

(87) PCT Pub. No.: WO2020/145831
PCT Pub. Date: Jul. 16, 2020

(65) Prior Publication Data
US 2022/0073461 A1    Mar. 10, 2022

(30) Foreign Application Priority Data
Jan. 7, 2019 (PL) .................................. P.428485

(51) Int. Cl.
C07D 403/06 (2006.01)
A61K 31/496 (2006.01)
A61P 25/04 (2006.01)
C07D 207/40 (2006.01)
C07D 207/416 (2006.01)
C07D 401/06 (2006.01)

(52) U.S. Cl.
CPC ............ C07D 207/40 (2013.01); *A61P 25/04* (2018.01); C07D 207/416 (2013.01); C07D 401/06 (2013.01)

(58) Field of Classification Search
CPC .. C07D 403/06; C07D 401/06; A61K 31/496; A61K 31/454; A61P 25/08; A61P 25/04; A61P 25/06; A61P 29/00
USPC .............. 544/372; 546/208; 514/254.01, 326
See application file for complete search history.

(56) References Cited

FOREIGN PATENT DOCUMENTS

| | | |
|---|---|---|
| WO | 03/094918 A1 | 11/2003 |
| WO | 2013/142307 A1 | 9/2013 |

OTHER PUBLICATIONS

Abram, M. et al.: Multifunctional hybrid compounds derived from 2-(2,5-dioxopyrrolidin-1-yl)-3-methoxypropaneamides with anticonvulsant and antinociceptive properties. J. Med. Chem., vol. 60, pp. 8565-8579, 2017.*

* cited by examiner

*Primary Examiner* — Charanjit Aulakh
(74) *Attorney, Agent, or Firm* — Mintz Levin Cohn Ferris Glovsky and Popeo, P.C.

(57) ABSTRACT

The first object of the invention is the compound of general formula (I) or pharmaceutically acceptable salts thereof. A second object of the invention is the use of compounds described by general formula (I) as active ingredient in pharmaceutical compositions for the treatment of epileptic seizures or neuropathic pain or migraine.

20 Claims, 9 Drawing Sheets

(I)

(II)

Figure 1:
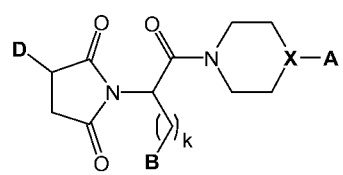
Figure 1:
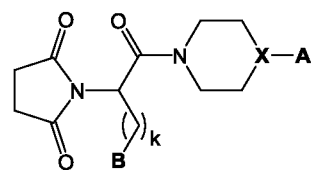

*i* - DCC, DCM, room temp., 4 h
*ii* - TFA, DCM, room temp., 2 h
*iii* - AcOEt, room temp., 30 min
*iv* - HMDS, ZnCl$_2$, benzene, reflux, 24 h
*v* - Ammonia, primary or secondary amine, benzene, room temp., 2 h

*i* - 100% CH$_3$COOH, 70°C, 12 h
*ii* - HMDS, ZnCl$_2$, benzene, reflux, 24 h
*iii* - CDI, DMF, room temp., 24 h

*i* - DCC, DCM, room temp., 4 h
*ii* - TFA, DCM, room temp., 2 h
*iii* - AcOEt, room temp., 30 min
*iv* - HMDS, ZnCl$_2$, benzene, reflux, 24 h Ogólny schemat syntezy enancjomerów związków wg wzoru (II).

*i* - DCC, DCM, room temp., 4 h
*ii* - TFA, DCM, room temp., 2 h
*iii* - AcOEt, room temp., 30 min
*iv* - HMDS, ZnCl$_2$, benzene, reflux, 24 h
*v* - Ammonia, primary or secondary amine, benzene, room temp., 2 h
*vi* - 2M HCl in MeOH Ogólny schemat syntezy rozpuszczalnych w wodzie soli związków wg wzoru (I).

(2,5-DIOXOPYRROLIDIN-1-YL)(PHENYL)-ACETAMIDE DERIVATIVES AND THEIR USE IN THE TREATMENT OF NEUROLOGICAL DISEASES

CROSS-REFERENCE TO RELATED APPLICATIONS

This application is a National Stage Entry of International Application No. PCT/PL2020/050001 filed Jan. 7, 2020, entitled "(2,5-DIOXOPYRROLIDIN-1-YL)(PHENYL)-ACETAMIDE DERIVATIVES AND THEIR USE IN THE TREATMENT OF NEUROLOGICAL DISEASES", and which claims priority to PL Application No. P.428485 filed Jan. 7, 2019 entitled "Pocbodne (2,5-dioksopirolidyn-1-ylo)(fenylo)-acetamidu i ich zastosowanie do leczenia chorób o podłożu neurologicznym."

The invention relates to (2,5-dioxopyrrolidin-1-yl)(phenyl)-acetamide derivatives and their pharmaceutically acceptable salts that are suitable for the treatment of neurological diseases. The disclosed compounds exhibit broad protective activity in animal models of epileptic seizures and pain models, and therefore may find application in the treatment of neurological diseases, in particular epilepsy and neuropathic pain. Due to the wide range of therapeutic indications for antiepileptic drugs, these compounds may also be useful, for example, for the treatment of migraine, withdrawal syndrome, schizophrenia, schizoaffective disorders, personality and nutrition disorders, as well as anxiety and post-traumatic stress.

Epilepsy is one of the most common neurological diseases associated with disturbance of excitability and neuronal conduction. This disease affects 1-2% of the human population and significantly reduces the patients' quality of life and the possibility of their daily functioning (Nadkarni, S.; LaJoie, J.; Devinsky, O. *Neurology* 2005, 64, S2-S11). Due to the complex pathophysiology, epilepsy is a heterogeneous disease, characterized by the occurrence of various types of seizures (including e.g. tonic-clonic, absence, partial, etc.) and significant drug resistance, reaching 30-40% of cases diagnosed (Kwan, P.; Schachter, S. C.; Brodie, M. J. *N. Engl. J. Med.* 2011, 365, 919-926). Neuropathic pain is another serious neurological disease, difficult from the therapeutic point of view. Current data indicate that only 50% of patients manage to achieve a 30-50% reduction in neuropathic pain sensation, while other patients fail to achieve improvement with any of the drugs used (Butera, J. A. *J. Med. Chem.* 2007, 11, 2543-2546). Therefore, there is a great need for new AEDs enabling the control of various types of epileptic seizures and preferably effective in neuropathic pain. Most of the currently used AEDs have a narrow range of therapeutic indications and therefore they are applicable only to a particular type of epileptic seizure. These drugs include among others the newest AEDs such as levetiracetam and lacosamide. Research carried out in recent years indicates that for the treatment of diseases with complex pathomechanism (so-called multifactorial diseases), multitargeted compounds, also known as multifunctional compounds, i.e. compounds with complex mechanism of molecular action, may be particularly beneficial. Combining of different and synergistic mechanisms enables a comprehensive therapeutic process, thus multitargeted substances seem to ensure increased therapeutic effectiveness compared to substances acting on a single biological target (Bansal, Y.; Silakari, O. *Eur. J. Med. Chem.* 2014, 76, 31-42). Another advantage of multifunctional drugs may be reduction of the number of drugs taken that may result in fewer and weaker intensity of adverse effects, lower risk of drug interactions and better cooperation between doctor and patient (compliance). It is also postulated that multitargeted compounds may be useful in the treatment of diseases characterized by high drug resistance (e.g. epilepsy) (Talevi, A. *Front. Pharmacol.* 2015, 6, 205). Multitargeted substances are usually designed as hybrid or chimeric molecules combining on common chemical scaffold structural fragments responsible for a specific pharmacological effect (Morphy, R.; Rankovic, Z. *J. Med. Chem.* 2005, 48, 6523-6543). Particularly intensive research on the development of multitargeted compounds as candidates for new drugs is carried out in the field of cancer, neurodegenerative and inflammatory diseases. Notably, the concept of molecular hybridization as a method allowing the design and development of new AEDs with a wide range of therapeutic indications has been recently proposed by present inventors (Abram, M.; Zagaja, M.; Mogilski, S.; Andres-Mach, M.; Latacz, G.; Baś, S.; Łuszczki, J. J.; Kieć-Kononowicz, K.; Kamiński, K. *J. Med. Chem.* 2017, 60, 8565-8579; Kamiński, K.; Zagaja, M.; Rapacz, A.; Łuszczki, J. J.; Andres-Mach, M.; Abram, M.; Obniska, J. *Bioorg. Med. Chem.* 2016, 24, 606-618; Kamiński, K.; Rapacz, A.; Filipek, B.; Obniska, J. *Bioorg. Med. Chem.* 2016, 24, 2938-2946; Kamiński, K.; Zagaja, M.; Łuszczki, J. J.; Rapacz, A.; Andres-Mach, M.; Latacz, G.; Kieć-Kononowicz, K. *J. Med. Chem.* 2015, 58, 5274-5286; Kamiński, K.; Rapacz, A.; Łuszczki, J. J.; Latacz, G.; Obniska, J.; Kieć-Kononowicz, K.; Filipek, B. *Bioorg. Med. Chem.* 2015, 23, 2548-2561).

Anticonvulsant and/or analgesic activity of new compounds is routinely evaluated in animal models (mainly in mice and rats). From a clinical point of view, particularly promising candidates for new broad-spectrum AEDs, effective in various types of human epileptic seizures, are substances active in the maximal electroshock test (MES), the subcutaneous pentylenetetrazole seizure test (scPTZ), and the psychomotor 6 Hz seizure model which utilizes low frequency current of 6 Hz (at the current intensity of 32 mA or/and 44 mA). Compounds with the aforementioned profile in preclinical in vivo studies may be effective in human tonic-clonic seizures with or without secondary generalization, generalized absence seizures, myoclonic seizures, partial seizures and drug-resistant epilepsy. The crucial add value of the above substances should be activity in important animal tests/models assessing antinociceptive activity, i.e. the formalin test, the capsaicin-induced pain model, and the oxaliplatin-induced neuropathic pain model.

The technical problem ahead the invention is to provide such chemical compounds that would be simple to obtain, would not show a hepatoxic effect and would be possible to use them, or their pharmaceutically acceptable salts, as active substances in pharmaceutical compositions to control various types of seizures (tonic-clonic seizures without or with secondary generalization, generalized absence seizures, myoclonic seizures, partial seizures and drug-resistant seizures), wherein such compounds should also have analgesic activity in pain with neuropathic origin or migraine.

The first object of the invention is a compound with the general formula (I) or pharmaceutically acceptable salts thereof,

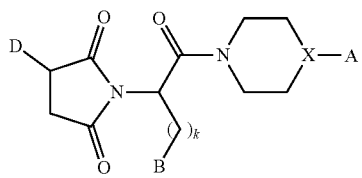

(I)

wherein:
X—is N or C,
k—is a number equal to 0 or 1,
A is a substituent selected from the group comprising of:
  phenyl substituent;
  phenyl substituent substituted with one or two or three or four side substituents selected from the group comprising of: halogen atoms, —$SCF_3$, —$CF_3$, —$CHF_2$, —CN, —$OCF_3$, —$NO_2$, —$OCH_3$, —$OC_2H_5$, an alkyl moiety with the number of carbon atoms in the carbon backbone from 1 to 4, wherein the alkyl moiety has a straight or branched chain;
  phenyl substituent substituted with at least one aromatic or heteroaromatic substituent;
  benzhydryl substituent;
  1-naphthyl or 2-naphthyl substituent;
  benzothiophenyl substituent selected from the group comprising of: 2-benzothiophenyl, 3-benzothiophenyl, 4-benzothiophenyl or 5-benzothiophenyl substituents, preferably 5-benzothiophenyl substituent;
  benzisoxazole substituent selected from the group comprising of: 3-benzisoxazole, 4-benzisoxazole, 5-benzisoxazole, 6-benzisoxazole, 7-benzisoxazole substituents, preferably 5-benzisoxazole substituent;
  alkyl moiety with the number of carbon atoms in the carbon backbone from 1 to 4, wherein the alkyl moiety has a straight or branched or cyclic chain, preferably the alkyl moiety is substituted with at least one halogen atom;
B is defined as:
  phenyl substituent;
  phenyl substituent substituted with one or two side substituents selected from the group comprising of: halogen atoms, —$SCF_3$, —$CF_3$, —$CHF_2$, —CN, —$OCF_3$, —$NO_2$, —$OCH_3$, —$OC_2H_5$, an alkyl moiety with the number of carbon atoms in the carbon backbone from 1 to 4, wherein the alkyl moiety has a straight or branched chain;
D is a substituent selected from the group comprising of:
  H, amino (—$NH_2$), amino group substituted with one or two aliphatic substituents (including in particular —$CH_3$ and/or —$C_2H_5$) or an amino group which is part of a heterocyclic ring.

The term "halogen" as used in the description of a compound according to general formula (I) includes fluorine, chlorine, bromine and iodine. In another preferred embodiment of the invention, the halogen atom is fluorine or chlorine.

The compound with the general formula (I) has chiral centers, thus it may exist in the form of optical isomers and mixtures thereof. The aformentioned optical isomers and mixtures thereof in various ratios, including racemic mixtures, are included in the scope of the invention. Individual isomers can be obtained using the appropriate isomeric forms of the starting material (amino acid derivatives) or can be separated after preparation of the final compound according to known separation methods.

Preferably, the compound of the invention is a compound with general formula (II) or its pharmaceutically acceptable salt,

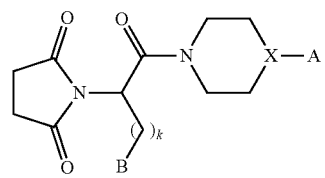

(II)

wherein:
X— is N or C,
k—is a number equal to 0 or 1,
A is a substituent selected from the group comprising of:
  phenyl substituent;
  phenyl substituent substituted with one or two or three or four side substituents selected from the group comprising of: halogen atoms, —$SCF_3$, —$CF_3$, —$CHF_2$, —CN, —$OCF_3$, —$NO_2$, —$OCH_3$, —$OC_2H_5$, an alkyl moiety with the number of carbon atoms in the carbon backbone from 1 to 4, wherein the alkyl moiety has a straight or branched chain;
  phenyl substituent substituted with at least one aromatic or heteroaromatic substituent;
  benzhydryl substituent;
  1-naphthyl or 2-naphthyl substituent;
  benzothiophenyl substituent selected from the group comprising of: 2-benzothiophenyl, 3-benzothiophenyl, 4-benzothiophenyl or 5-benzothiophenyl substituents, preferably 5-benzothiophenyl substituent;
  benzisoxazole substituent selected from the group comprising of: 3-benzisoxazole, 4-benzisoxazole, 5-benzisoxazole, 6-benzisoxazole, 7-benzisoxazole substituents, preferably 5-benzisoxazole substituent;
  alkyl moiety with the number of carbon atoms in the carbon backbone from 1 to 4, wherein the alkyl moiety has a straight or branched or cyclic chain, preferably the alkyl moiety is substituted with at least one halogen atom;
B is:
  phenyl substituent;
  phenyl substituent substituted with one or two side substituents selected from the group comprising of: halogen atoms, —$SCF_3$, —$CF_3$. —$CHF_2$, —CN, —$OCF_3$, —$NO_2$, —$OCH_3$, —$OC_2H_5$, an alkyl moiety with the number of carbon atoms in the carbon backbone from 1 to 4, wherein the alkyl moiety has a straight or branched chain;

Preferably, the halogen atom is a fluorine or chlorine atom.

Preferably, the alkyl moiety in the carbon backbone contains from 1 to 4 carbon atoms, wherein the alkyl moiety has a straight or branched chain, and is selected from the group comprising of: methyl, ethyl, propyl, isopropyl, n-butyl, sec-butyl, tert-butyl substituents.

The compound with the general formula (II) has a chiral center, therefore it may exist in the form of optical isomers and mixtures thereof. The aformentioned optical isomers and mixtures thereof in various ratios, including racemic mixtures, are included in the scope of the invention. Individual isomers can be obtained using the appropriate isomeric forms of the starting material (amino acid derivatives) or can be separated after preparation of the final compound according to known separation methods.

Preferably, k=0.

Preferably, the X atom is a nitrogen atom.

Preferably, substituent A is selected from the group comprising of: 5-benzothiophenyl, 2-naphthyl, 5-benzisoxazolyl substituents.

Preferably, A is selected from the group comprising of: phenyl, phenyl substituted with at least one chlorine or —CF$_3$, —CHF$_2$, —OCF$_3$, —CH$_3$, —SCF$_3$ or phenyl.

Preferably, the substituent B is selected from the group comprising of: phenyl or phenyl substituted with one or two halogen atoms.

Preferably, the compound of the invention is selected from the group comprising of:

1-(2-Oxo-1-phenyl-2-(4-phenylpiperazin-1-yl)ethyl)pyrrolidine-2,5-dione 1-(2-(4-(3-Chlorophenyl)piperazin-1-yl)-2-oxo-1-phenylethyl)pyrrolidine-2,5-dione 1-(2-(4-(3,5-Dichlorophenyl)piperazin-1-yl)-2-oxo-1-phenylethyl)pyrrolidine-2,5-dione 1-(2-Oxo-1-phenyl-2-(4-(m-tolyl)piperazin-1-yl)ethyl)pyrrolidine-2,5-dione 1-(2-Oxo-1-phenyl-2-(4-(3-(trifluoromethyl)phenyl)piperazin-1-yl)ethyl)pyrrolidine-2,5-dione 1-(2-Oxo-1-phenyl-2-(4-(4-(trifluoromethyl)phenyl)piperazin-1-yl)ethyl)pyrrolidine-2,5-dione 1-(2-(4-(3,5-Bis(trifluoromethyl)phenyl)piperazin-1-yl)-2-oxo-1-phenylethyl)pyrrolidine-2,5-dione 1-(2-Oxo-1-phenyl-2-(4-(3-(difluoromethyl)phenyl)piperazin-1-yl)ethyl)pyrrolidine-2,5-dione 1-(2-Oxo-1-phenyl-2-(4-(3-(trifluoromethoxy)phenyl)piperazin-1-yl)ethyl)pyrrolidine-2,5-dione 1-(2-Oxo-1-phenyl-2-(4-(4-(trifluoromethoxy)phenyl)piperazin-1-yl)ethyl)pyrrolidine-2,5-dione 1-(2-Oxo-1-phenyl-2-(4-(3-(trifluoromethyl(sulfanyl)phenyl)piperazin-1-yl)ethyl)pyrrolidine-2,5-dione 1-(2-(4-([1,1'-Biphenyl]-3-yl)piperazin-1-yl)-2-oxo-1-phenylethyl)pyrrolidine-2,5-dione 1-(1-(4-Fluorophenyl)-2-oxo-2-(4-(3-(trifluoromethyl)phenyl)piperazin-1-yl)ethyl)pyrrolidine-2,5-dione 1-(2-(4-(Naphth-2-yl)piperazin-1-yl)-2-oxo-1-phenylethyl)pyrrolidine-2,5-dione 1-(2-(4-(Benzo[b]thiophen-5-yl)piperazin-1-yl)-2-oxo-1-phenylethyl)pyrrolidine-2,5-dione 1-(2-(4-(1,2-Benzoxazol-5-il)piperazin-1-yl)-2-oxo-1-phenylethyl)pyrrolidine-2,5-dione 1-(2-(4-(3-Chlorophenyl)piperidin-1-yl)-2-oxo-1-phenylethyl)pyrrolidine-2,5-dione 1-(2-Oxo-1-phenyl-2-(4-(3-(trifluoromethyl)phenyl)piperidin-1-yl)ethyl)pyrrolidine-2,5-dione 1-(2-Oxo-1-phenyl-2-(4-(3-(trifluoromethoxy)phenyl)piperidin-1-yl)ethyl)pyrrolidine-2,5-dione.

Preferably, the compound of the invention is a (R) enantiomer, preferably selected from the following compounds:

(R)-1-(2-(4-(3-chlorophenyl)piperazin-1-yl)-2-oxo-1-phenylethyl)pyrrolidine-2,5-dione, (R)-1-(2-(4-(3,5-dichlorophenyl)piperazin-1-yl)-2-oxo-1-phenylethyl)pyrrolidine-2,5-dione, (R)-1-(2-oxo-1-phenyl-2-(4-(3-(trifluoromethyl)phenyl)piperazin-1-yl)ethyl)pyrrolidine-2,5-dione, (R)-1-(2-oxo-1-phenyl-2-(4-(3-(trifluoromethoxy)phenyl)piperazin-1-yl)ethyl)pyrrolidine-2,5-dione, (R)-1-(2-oxo-1-phenyl-2-(4-(3-(trifluoromethyl(sulfanyl)phenyl)piperazin-1-yl)ethyl)pyrrolidine-2,5-dione.

Preferably, the compound of the invention is a water-soluble salt, especially a hydrochloride salt, preferably selected from the following compounds:

3-(Methylamino)-1-(2-oxo-1-phenyl-2-(4-(3-(trifluoromethyl)phenyl)piperazin-1-yl)ethyl)pyrrolidine-2,5-dione hydrochloride, 3-(Dimethylamino)-1-(2-oxo-1-phenyl-2-(4-(3-(trifluoromethyl)phenyl)piperazin-1-yl)ethyl)pyrrolidine-2,5-dione hydrochloride, 3-(Diethylamino)-1-(2-oxo-1-phenyl-2-(4-(3-(trifluoromethyl)phenyl)piperazin-1-yl)ethyl)pyrrolidine-2,5-dione hydrochloride.

A second object of the invention is a compound according to the invention, as defined above, for use in the treatment or prevention of epileptic seizures, neuropathic pain or migraine. In a preferred embodiment, the compound according to the invention is used as the active substance (the only one or one of many) contained in a pharmaceutical composition for the treatment or prevention of at least one of the above medical indications.

The compounds according to the invention possess anticonvulsant and analgesic activity in a wide panel of animal models and may find application as active substances in various dosage forms for the treatment of epilepsy and neuropathic pain.

Figure 2A:
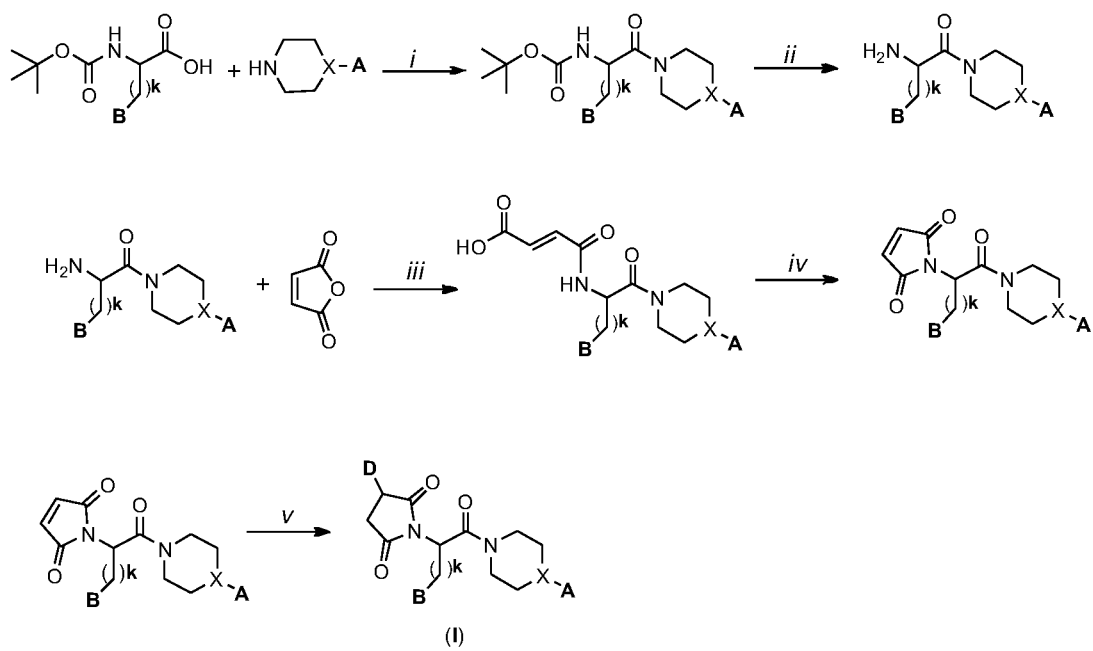
Figure 2B:
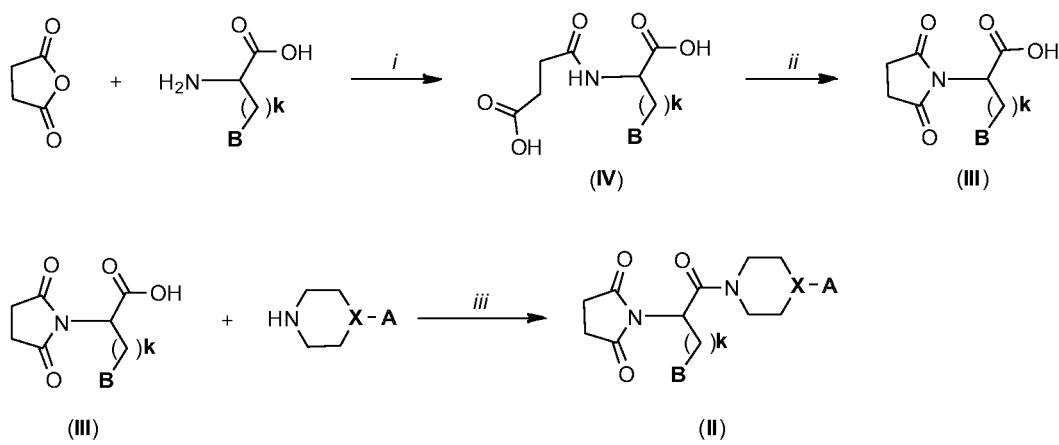

The compounds of formula (I) according to the invention can be obtained using a multi-step synthetic procedure, which is illustrated in FIG. 2A, where X, A, B, D and k are as defined above. For the preparation of compounds of formula (I), where D is hydrogen, the procedure described for compounds of formula (II) according to FIG. 2B is used. In the first stage, as a result of the condensation reaction (i) of the appropriate piperazine derivative with the corresponding tert-butoxycarbonyl (Boc) amino acid derivative, an intermediate product with amide structure is obtained, which then undergoes deprotection reaction (ii) to form an amine derivative. In the next step, the aforementioned amine derivative is subjected to condensation reaction (iii) with maleic anhydride, resulting in unsaturated amido-acid derivative. This derivative forms the corresponding maleimide applying the cyclization reaction (iv). In the next step (v), the maleimide derivative is subjected to the addition reaction with the appropriate primary or secondary amine to obtain a compound with the general formula (I) according to the invention.

Compounds of formula (II) according to the invention can be obtained starting from a compound of formula (III):

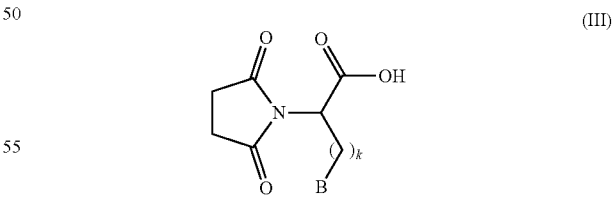

(III)

wherein B and k are defined as for formula (II). The compound of formula (III) can be obtained in the two-step procedure using commercially available succinic anhydride and the corresponding amino acid derivatives as substrates. In the first step, as a result of the condensation reaction of succinic anhydride with the appropriate amino acid, an intermediate product with the amido-acid structure (IV) is obtained, which then, undergoes the cyclization reaction to form the desired compound with formula (III). Alternatively, the compound described by formula (III) can be prepared by using a one-step thermal cyclocondensation reaction between succinic anhydride or succinic acid and the corresponding amino acid.

The desired compounds with general formula (II) according to the invention can be obtained by using an amidation reaction between the compound described by formula (III) and suitable commercially available secondary aliphatic amine. This reaction can be carried out in the presence of known coupling agents, including CDI, EDCI, DCC, etc. Alternatively, the compounds of formula (II) can be obtained by reaction between the acid chloride resulting from the transformation of the carboxylic acid described by formula (II) and the corresponding commercially available secondary aliphatic amine. The compounds described by formula (II) according to the invention can also be prepared in the reaction between the carboxylic acid and the corresponding aliphatic amine using activating agents selected from BOP, HBTU, HATU in the presence of an organic base, especially triethylamine (TEA), N-methylmorpholine (NMM) or N,N-diisopropylethylamine (DIEA).

The synthetic procedure and reaction conditions are illustrated in FIG. 2B, where X, A, B and k are as defined above.

The solution according to the invention has several advantages. The disclosed compounds of formula (I), preferably compounds of formula (II), are characterized by strong and broad anticonvulsant activity in various animal models of epilepsy, i.e. the maximal electroshock seizure test (MES), the subcutaneous pentylenetetrazole seizure test (scPTZ), and the 6 Hz seizure model (32 mA and/or 44 mA). Compounds with the aforementioned profile in the preclinical in vivo studies can be effective in various types of human epilepsy, including tonic-clonic seizures with or without secondary generalization, generalized seizures (absence), myoclonic seizures, partial seizures, and importantly drug-resistant seizures. Another advantage of compounds with general formula (I), especially compounds described by formula (II), is a strong analgesic activity in animal models assessing the antinociceptive activity, i.e., the formalin test, the capsaicin-induced pain model, and the oxaliplatin-induced neuropathic pain model. For this reason, compounds of formula (I), preferably compounds of formula (II), may be useful in the treatment of pain with both neurogenic and inflammatory origin, which is an unique feature among AEDs available in the pharmacotherapy. Compounds according to formula (I), preferably formula (II), have a complex mechanism of molecular action, namely they interact with voltage-dependent sodium channels, calcium channels and TRPV1 receptor. The beneficial antagonist effect observed in the case of TRPV1 receptor has not been proven for known and therapeutically relevant AEDs yet. Importantly, literature data suggest a possible involvement of TRPV1 in the induction of seizures (Nazıroğlu, M. *Curr. Neuropharmacol.* 2015, 13, 239-247; Nazıroğlu, M.; Övey, I. S. *Neuroscience* 2015, 293, 55-66), while its role as a molecular target for substances with anti-nociceptive activity is well documented (Szallasi, A.; Cortright, D. N.; Blum, C. A.; Eid, S. R. *Nat. Rev. Drug. Discov.* 2007, 6, 357-372). Compounds according to formula (II) can also be potentially useful, among others for the treatment of withdrawal syndrome, schizophrenia, schizoaffective disorder, personality and nutrition disorders, as well as anxiety and post-traumatic stress. Therefore, the present invention provides compounds for the use as drugs. Furthermore, the possibility of using TRPV1 receptor antagonists to treat various types of epileptic seizures is disclosed.

The compounds according to the invention may be administered by a variety of routes, including enteral, topical or parenteral administration, applying suitable pharmaceutical preparation for given administration route and containing at least one active compound according to formula (I), preferably formula (II), in pharmaceutically acceptable and effective amounts together with pharmaceutically acceptable diluents, carriers and/or excipients known in the art. The methodology for the preparation of such pharmaceutical formulations is known in the art. The therapeutic dose will vary depending on the substance, species, sex, age, disease entity being treated, route and method of administration, which must be determined by a specialist in the field. The proposed dose of compounds according to the invention is from 0.1 to about 1000 mg per day, in single or divided doses. The compounds of the invention are administered to a patient as such or in combination with one or more other active ingredients each in its own composition or some or all of the active ingredients combined in a single composition, and/or appropriate pharmaceutical excipients. Suitable pharmaceutical excipients include conventional supporting substances required for proper preparation of given formulation, such as fillers, binders, disintegrants, lubricants, solvents, gel formers, emulsifiers, stabilizers, dyes and/or preservatives. The compounds of the invention are formulated into dosage forms using commonly known pharmaceutical methods of preparation. Dosage forms can be, e.g., tablets, capsules, granules, suppositories, emulsions, suspensions or solutions. Depending on the method of administration and the galenical form, the amount of active substance in the formulation may typically range from 0.01% and 100% (by weight).

Figure 3:
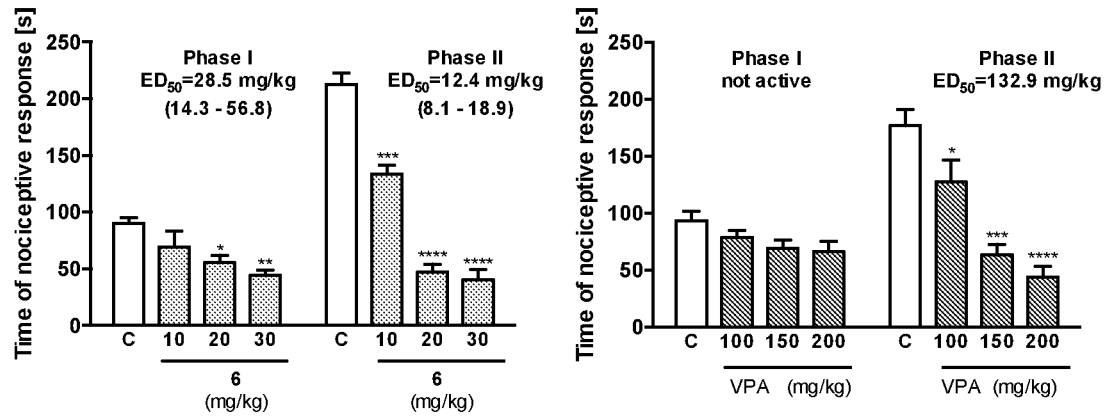
Figure 4:
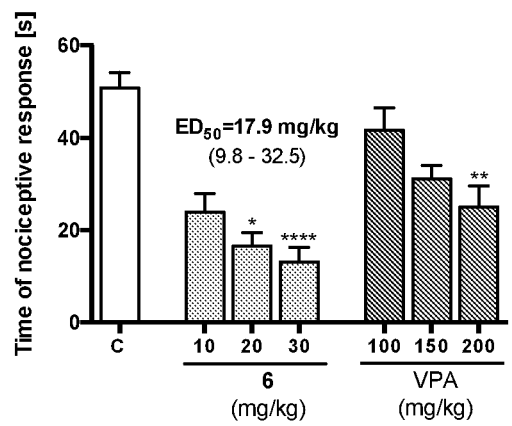
Figure 5:
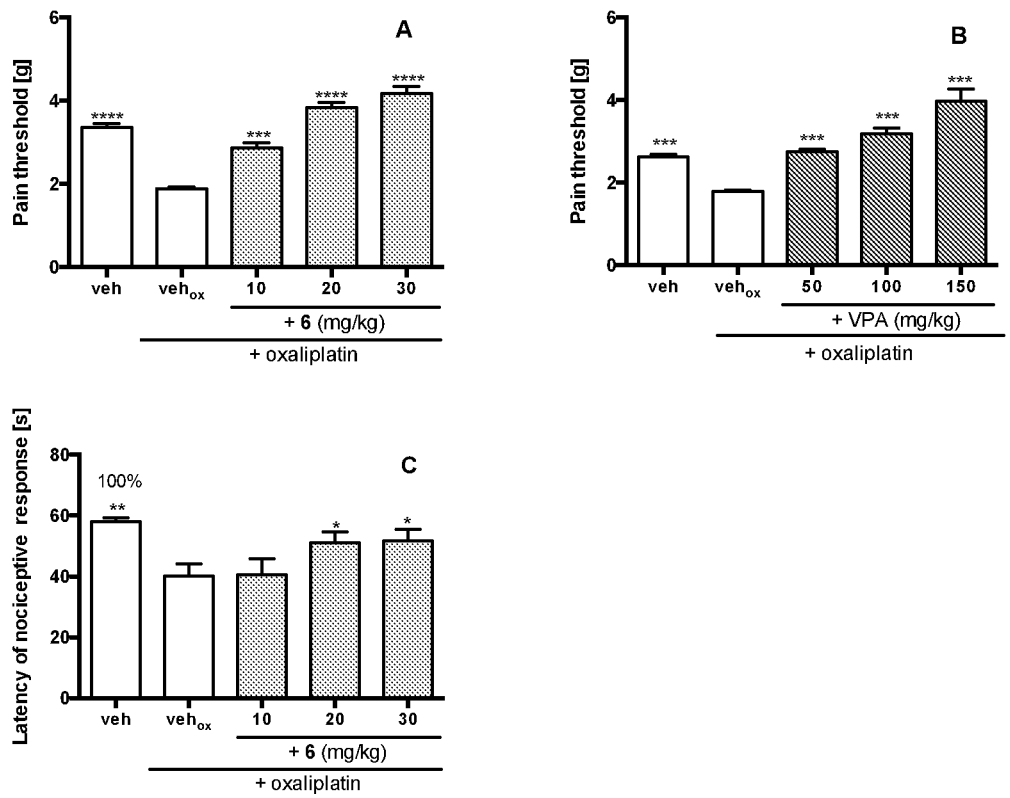
Figure 6:
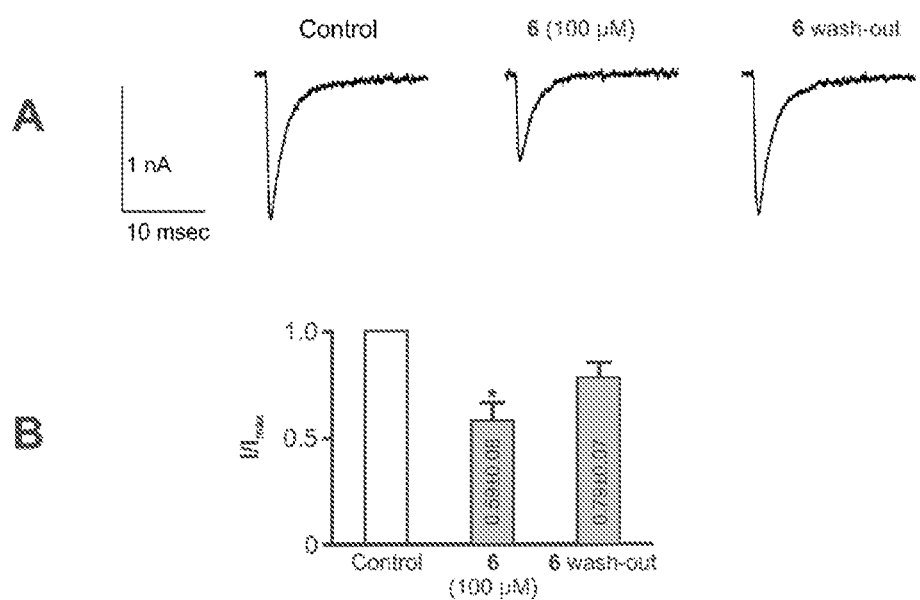
Figure 7:
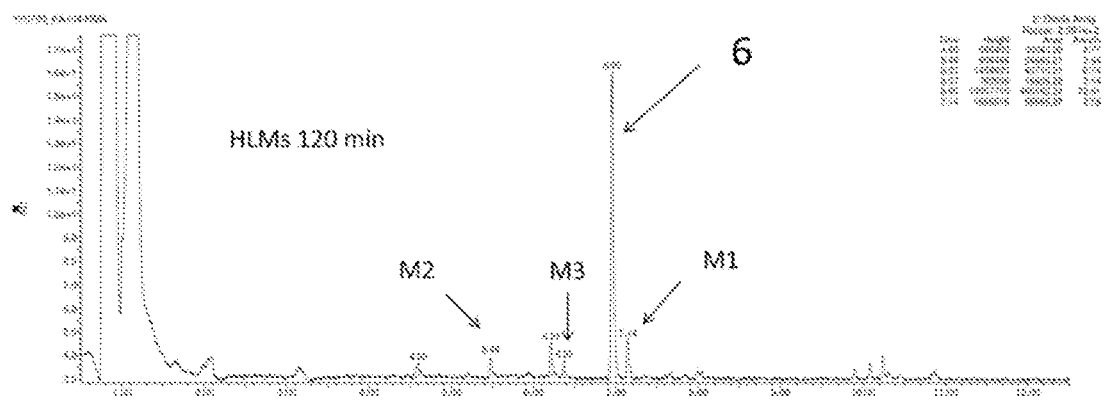
Figure 8:
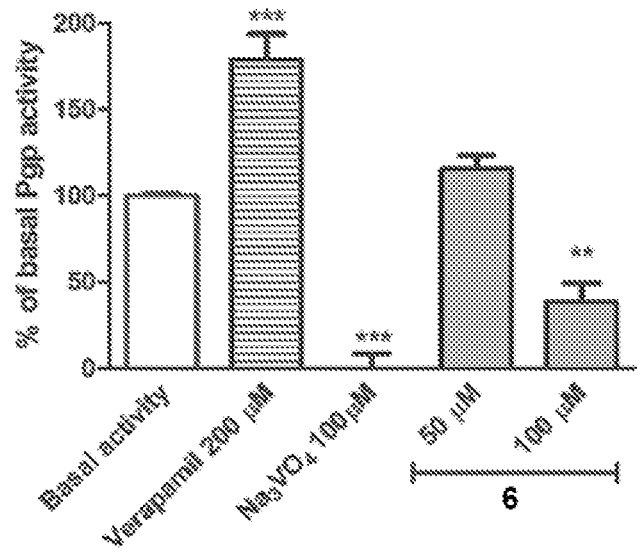
Figure 9:
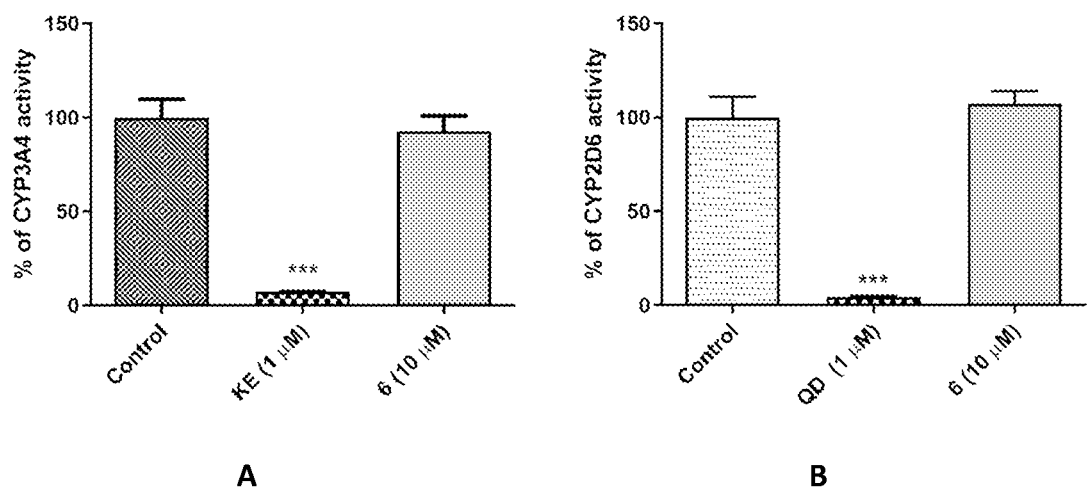
Figure 10:
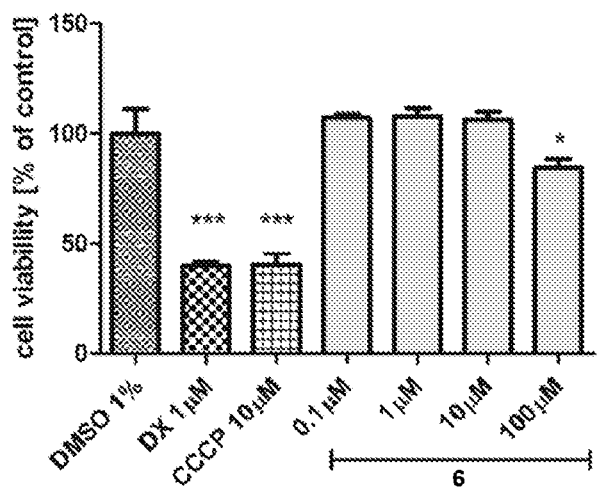
Figure 11:
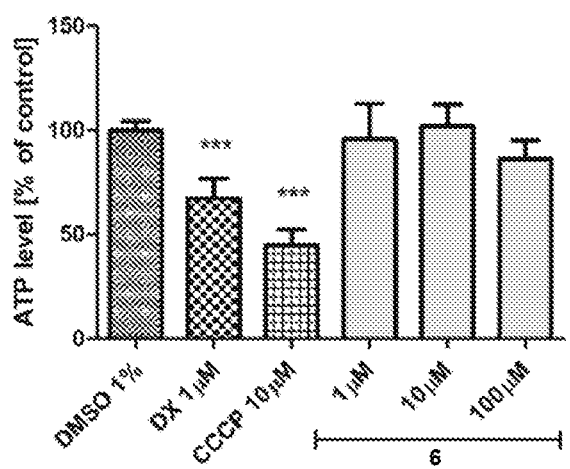
Figure 12:
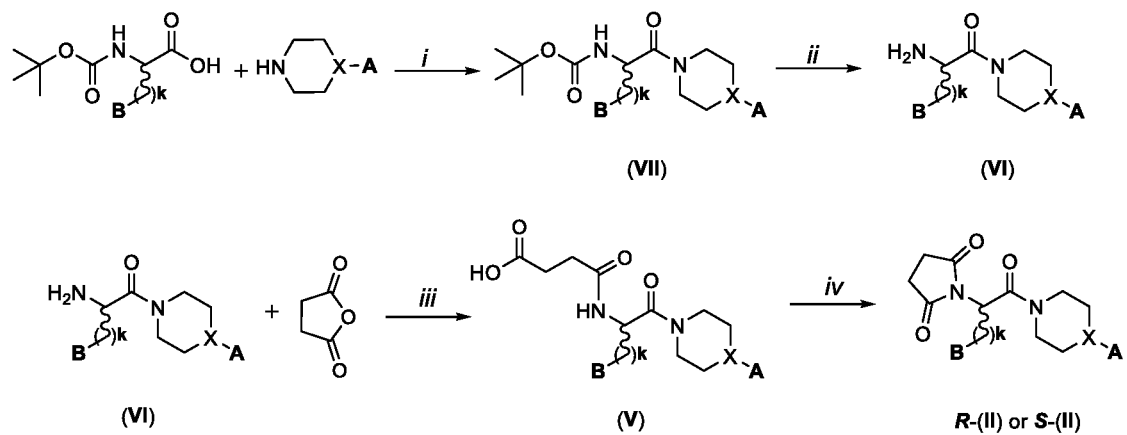
Figure 13:
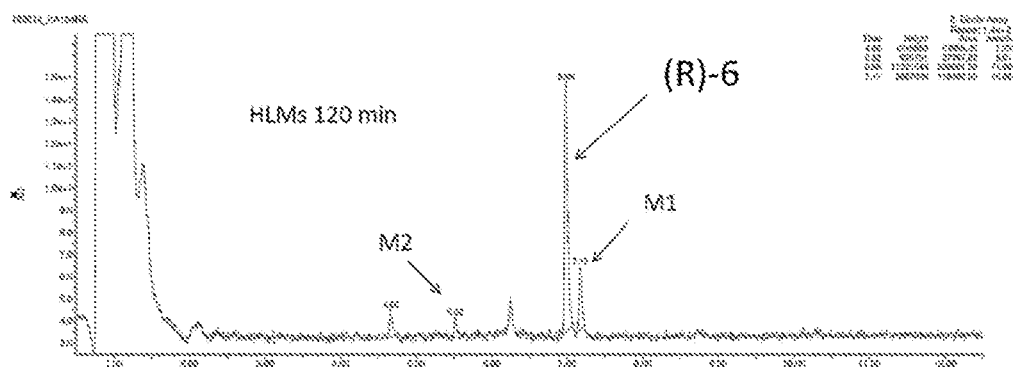
Figure 14:
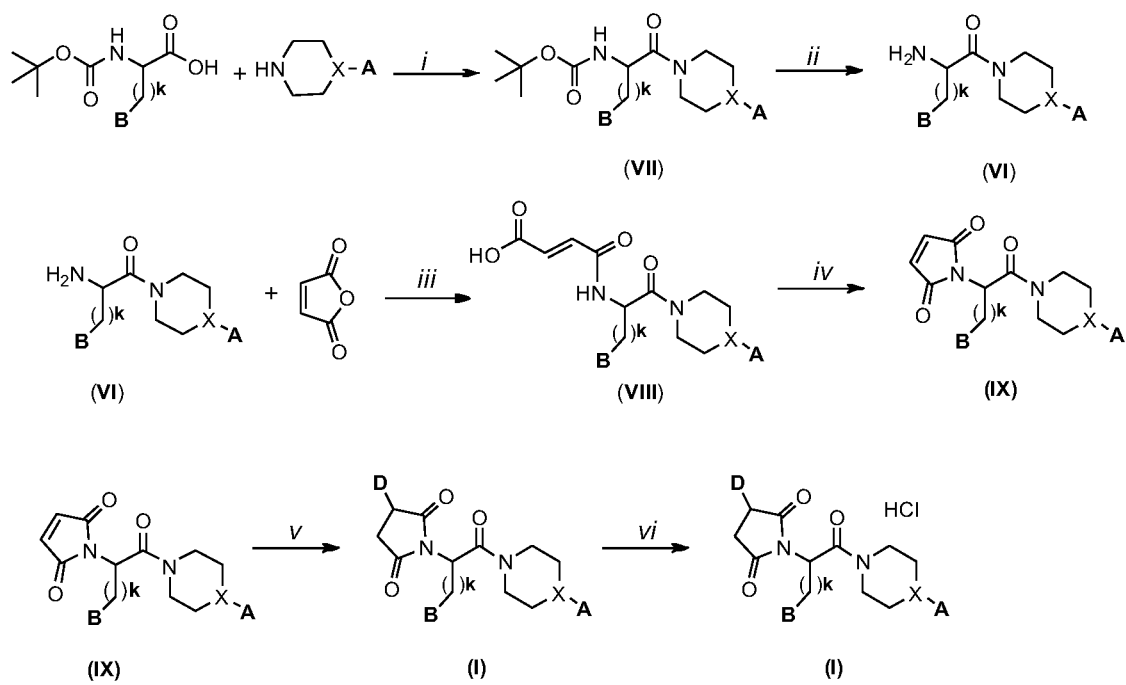

Embodiments of the invention are illustrated in Figures, where it is shown:

FIG. 1—general formula of compound (I) and (II);

FIG. 2A—the synthesis of derivatives according to formula (I);

FIG. 2B—the synthesis of derivatives according to formula (II);

FIG. 3—analgesic activity of compound 6 and valproic acid (VPA) in phase I and II pain of the formalin test, where the results are presented as time of paw licking in the first phase of the test (0-5 minutes after formalin injection) and in phase II (15-30 minutes after formalin injection), the values represent mean±SEM for a group of 8-10 animals; statistically significant difference in comparison to the control (vehicle—Tween) group, statistical analysis—one-way ANOVA analysis of variance, Dunnett's post hoc test: *$p<0.05$, $p<0.01$, *$p<0.001$, ****$p<0.0001$. C—control group; VPA—valproic acid;

FIG. 4—analgesic activity of compound 6 and valproic acid (VPA) in the capsaicin assay, where the results are shown as paw licking time 0-5 minutes after capsaicin injection, the values represent mean±SEM; statistically significant difference in comparison to the control (vehicle—Tween) group, statistical analysis—one-way ANOVA analysis of variance, Dunnett's post hoc test: *$p<0.05$, $p<0.01$, **$p<0.0001$. C—control group; VPA—valproic acid;

FIG. 5—analgesic activity of compound 6 and valproic acid (VPA) in the oxaliplatin-induced peripheral neuropathy, where: A—the effect of compound 6 on mechanical allodynia in the von Frey test. B—the effect of valproic acid (VPA) on mechanical allodynia in the von Frey test. C—the effect of compound 6 on thermal allodynia in the Cold Plate test, the results are presented as the mean value of pressure force causing paw lift (von Frey test) or latency time to the occurrence of the nociceptive cold-plate reaction ±SEM for in group of 8-10 animals; statistically significant difference compared to the control group (mice after administration of OXPT and before administration of test compounds, statistical analysis—one-way ANOVA analysis of variance, Dunnett's post hoc test: *p<0.05, p<0.01, *p<0.001, ****p<0.0001. Veh—vehicle (1% Tween 80);

FIG. 6—the effect of compound 6 (at a concentration of 100 μM) on fast, potential-dependent sodium currents, where: A—example traces of maximal voltage-gated sodium currents in control, in the presence of compound 6 and after wash-out of compound 6; B—averaged normalized current amplitudes in control, in the presence of the compound 6 (*p<0.001, ANOVA with Tukey's test), and after wash-out of compound 6. I/Imax (on the vertical axis) means that the currents were normalized to control values;

FIG. 7—UPLC analysis of the metabolism of compound 6 after incubation with HMLs;

FIG. 8—the effect of verapamil, $Na_3VO_4$ and compound 6 on baseline Pgp activity, statistical significance were calculated by one-way ANOVA variance analysis and the Bonferroni method (p<0.01, *p<0.001, compounds tested in triplicate);

FIG. 9A—effect of the reference inhibitor ketoconazole (KE) and compound 6 on CYP3A4 activity; B—the effect of the reference inhibitor quinidine (QD) and 6 on CYP2D6 activity. Statistical significance was calculated by one-way ANOVA variance analysis and the Bonferroni method (***p<0.001);

FIG. 10—effect of reference cytostatic doxorubicin (DX), mitochondrial toxin CCCP (carbonyl cyanide m-chlorophenylhydrazone) and compound 6 on cell viability of the HepG2 line after 72 h incubation. Statistical significance was calculated by one-way ANOVA variance analysis and the Bonferroni method (*p<0.05, ***p<0.001, compounds tested in four replications);

FIG. 11—ATP level in HepG2 cell line after 3 hours incubation. Doxorubicin (DX), CCCP (carbonyl cyanide m-chlorophenylhydrazone). Statistical significance was calculated by one-way ANOVA variance analysis and the Bonferroni method (***p<0.001, compounds tested in four replications);

FIG. 12—general scheme for the synthesis of enantiomers of compounds according to formula (II);

FIG. 13—UPLC analysis of (R)-6 enantiomer metabolism after incubation with HMLs;

FIG. 14—general scheme for the synthesis of water-soluble salts of compounds according to formula (I).

ANALYTICAL METHODS

Proton magnetic resonance ($^1$H NMR) and carbon nuclear magnetic resonance ($^{13}$C NMR) spectra were recorded using a Mercury-300 "Varian" spectrometer (Varian Inc., Palo Alto, CA, USA) at 300 MHz and 75 MHz, respectively, or JEOL-500 spectrometer (JEOL USA, Inc. MA, USA), operating at 500 MHz and 126 MHz, respectively. Chemical shifts are given in δ (ppm) values relative to TMS δ=0 (1H) as an internal standard. J values are expressed in hertz (Hz). Deuterated chloroform ($CDCl_3$) or deuterated dimethyl sulfoxide (DMSO-$D_6$) was used as the solvent. The following signal abbreviations have been used in the spectra description: s (singlet), br s (broad singlet), d (doublet), dd (doublet of doublets), ddd (doublet of doublet of doublets), t (triplet), td (triplet of doublets), q (quartet), m (multiplet). The UPLC/MS analysis system consisted of a Waters ACQUITY® UPLC® apparatus (Waters Corporation, Milford, MA, USA) coupled with a Waters TQD mass spectrometer operating in electrospray ionization (ESI) mode. Chromatographic separations were carried out using the Acquity UPLC BEH C18, 1.7 μm (2.1×100 mm) column with the VanGuard Acquity UPLC BEH C18, 1.7 μm (2.1×5 mm) (Waters, Milford, CT, USA). The column was maintained at 40° C. and eluted with a gradient of 95% to 0% of eluent A over 10 min, with a flow rate of 0.3 mL/min. Eluent A: water/formic acid (0.1%, v/v); eluent B: acetonitrile/formic acid (0.1%, v/v). Chromatograms were recorded using a Waters eλ PDA detector. Spectra were analyzed in the 200-700 nm range with a resolution of 1.2 nm and a sampling rate of 20 points/s. he UPLC retention times ($t_R$) are given in minutes. Thin layer chromatography (TLC) was performed on aluminum sheets coated with silica gel 60 $F_{254}$ (Macherey-Nagel, Düren, Germany), using developing solvent systems with the following composition: DCM:MeOH (9:0.2; v/v), DCM:MeOH (9:0.3; v/v), DCM:MeOH (9:0.5; v/v), DCM:MeOH (9:1, v/v). Spot detection—UV light (λ=254 nm). Melting points (m.p.) were determined using open capillaries in a Büchi 353 apparatus (Büchi Labortechnik, Flawil, Switzerland). Enantiomeric purity was determined using a chiral HPLC technique on a Shimadzu Prominence and LC-2030C SD Plus apparatus (Shimadzu Corporation, Kyoto, Japan) equipped with an Amylose-C (250×4.6 mm) chiral column. The analysis was performed under the following conditions: column temperature: 20° C., mixture of eluents: hexane/i-PrOH=80/20 (v/v), flow: 1 mL/min, detection at the wavelength λ=206 nm. Enantiomeric purity is expressed in %.

The preparation of compounds of the invention is illustrated in the following examples. The syntheses presented in the examples below were not optimized in terms of yield, amount of reagents used or the final form of obtained compounds.

Abbreviations used:
AcOEt—ethyl acetate
CDI—carbonyldiimidazole
DCC—N,N'-dicyclohexylcarbodiimide
DCM—dichloromethane
DMF—dimethylformamide
$Et_2O$—diethyl ether
HCl—hydrochloric acid
HMDS—hexamethyldisilazane
MeOH—methanol
NaCl—sodium chloride
$Na_2SO_4$— sodium sulfate
$ZnCl_2$— zinc chloride Example 1. Synthesis, Physicochemical and Spectral Data of Intermediates (IV and III According to the Scheme in FIG. 2B)

Intermediate IV:
4-((Carboxy(phenyl)methyl)amino)-4-oxobutanoic acid

Succinic anhydride (3.0 g, 30 mmol, 1 eq) was dissolved in 15 mL of glacial acetic acid, followed by the addition of an equimolar amount of DL-phenylglycine (4.53 g). The mixture was heated at 70° C. with stirring for 12 hours. After this time, acetic acid was distilled off to dryness. Intermediate IV was obtained as a solid after washing with $Et_2O$.

White solid. Yield: 87% (6.55 g); m.p. 199.4-200.6° C.; TLC: $R_f$=0.25 (DCM:MeOH (9:1; v/v)); $C_{12}H_{13}NO_5$ (251.24), Monoisotopic mass: 251.08. UPLC (100% purity): $t_R$=2.77 min. (M+H)$^+$ 252.1.

Intermediate III:
2-(2,5-Dioxopyrrolidin-1-yl)-2-phenylacetic acid

ZnCl$_2$ (2.73 g, 20 mmol, 1 eq) was added to a suspension of 4-((carboxy(phenyl)methyl)amino)-4-oxobutanoic acid (5.0 g, 20 mmol, 1 eq) (IV) in dry benzene (100 mL) and heated to 80° C. Then a solution of HMDS (4.84 g, 6.25 mL, 30 mmol, 1.5 eq) in dry benzene (15 mL) was added dropwise over 30 minutes. The reaction was continued with stirring at reflux for about 24 hours and next concentrated under reduced pressure. After removal off the solvent, the oily residue was dissolved in DCM and extracted with 0.1 M HCl (3×50 mL), water (3×50 mL) and saturated NaCl solution (3×50 mL). The organic layer was dried over anhydrous Na$_2$SO$_4$ and then evaporated to dryness. 2-(2,5-Dioxopyrrolidin-1-yl)-2-phenylacetic acid was obtained as a solid substance after washing with Et$_2$O. Alternatively, 1,4-dioxane can be used instead of benzene in the above procedure.

White solid. Yield: 90% (4.20 g); m.p. 195.5-198.2° C.; TLC: R$_f$=0.45 (DCM:MeOH (9:1; v/v)); C$_{12}$H$_{11}$NO$_4$ (233.22), Monoisotopic mass: 233.07. UPLC (100% purity): t$_R$=3.41 min. (M+H)$^+$ 234.1. $^1$H NMR (300 MHz, DMSO-D$_6$) δ 2.73 (s, 4H), 5.76 (s, 1H), 7.26-7.35 (m, 3H), 7.36-7.45 (m, 2H), 13.22 (br s, 1H).

Example 2. 1-(2-Oxo-1-phenyl-2-(4-phenylpiperazin-1-yl)ethyl)pyrrolidine-2,5-dione Carbonyldiimidazole (1.17 g, 7.2 mmol, 1.2 eq) was dissolved in 5 mL of dry DMF and then added to a solution of 2-(2,5-dioxopyrrolidin-1-yl)-2-phenylacetic acid (1.40 g, 6 mmol, 1 eq) dissolved in 10 mL of anhydrous DMF. After stirring for 0.5 hour, a solution of 1-phenylpiperazine (0.97 g, 6 mmol, 1 eq) in 5 mL of anhydrous DMF was added dropwise. The reaction was continued with stirring at room temperature for 24 hours. After this time, DMF was distilled off under reduced pressure. The crude product was purified by column chromatography using mixture of DCM:MeOH (9:0.3; v/v) as solvent system. The compound was obtained as a solid after washing with Et$_2$O.

White solid. Yield: 84% (1.90 g); m.p. 156.7-157.4° C.; TLC: R$_f$=0.35 (DCM:MeOH (9:0.3; v/v)); C$_{22}$H$_{23}$N$_3$O$_3$ (377.44), Monoisotope mass: 377.17. UPLC (100% purity): t$_R$=5.88 min. (M+H)$^+$ 378.1. $^1$H NMR (300 MHz, CDCl$_3$) δ 2.58-2.81 (m, 5H), 2.95-3.15 (m, 2H), 3.17-3.42 (m, 3H), 3.63-3.76 (m, 1H), 3.92-4.05 (m, 1H), 6.12 (s, 1H), 6.80-6.91 (m, 3H), 7.19-7.28 (m, 2H) 7.29-7.47 (m, 5H); $^{13}$C NMR (75 MHz, CDCl$_3$) δ 28.1, 42.4, 45.8, 48.9, 49.2, 56.8, 116.5, 116.6, 120.6, 128.6, 128.9, 129.1, 129.2, 129.8, 129.9, 133.0, 150.7, 165.0, 176.3.

Example 3. 1-(2-(4-(3-Chlorophenyl)piperazin-1-yl)-2-oxo-1-phenylethyl)pyrrolidine-2,5-dione The compound was prepared according to procedure described in Example 2. 2-(2,5-Dioxopyrrolidin-1-yl)-2-phenylacetic acid (1.40 g, 6 mmol, 1 eq) and 1-(3-chlorophenyl) piperazine (1.40 g, 6 mmol, 1 eq) were used as starting materials. The crude product was purified by column chromatography using DCM:MeOH (9:0.2; v/v) eluent system.

White solid. Yield: 81% (2.00 g); m.p. 128.1-129° C.; TLC: R$_f$=0.51 (DCM:MeOH (9:0.2; v/v)); C$_{22}$H$_{22}$ClN$_3$O$_3$ (411.89), Monoisotopic mass: 411.13. UPLC (100% purity): t$_R$=6.69 min, (M+H)$^+$ 412.1. $^1$H NMR (300 MHz, CDCl$_3$) δ 2.58-2.73 (m, 4H), 3.00 (br s, 1H), 3.27-3.53 (m, 3H), 3.54-3.86 (m, 2H), 4.17 (br s, 2H), 6.02 (s, 1H), 7.27-7.40 (m, 7H), 7.51-7.63 (m, 2H); $^{13}$C NMR (75 MHz, CDCl$_3$) δ 28.0, 40.0, 43.3, 53.3, 53.7, 56.5, 118.9, 120.8, 128.9, 129.1, 129.3, 129.6, 131.4, 132.1, 135.9, 143.8, 165.5, 176.7.

Example 4. 1-(2-(4-(3,5-Dichlorophenyl)piperazin-1-yl)-2-oxo-1-phenylethyl)pyrrolidine-2,5-dione The compound was prepared according to procedure described in Example 2. 2-(2,5-dioxopyrrolidin-1-yl)-2-phenylacetic acid (1.40 g, 6 mmol, 1 eq) and 1-(3,5-dichlorophenyl)piperazine (1.20 g, 6 mmol, 1 eq). The crude product was purified by column chromatography using DCM:MeOH (9:0.3; v/v) eluent system.

White solid. Yield: 77% (2.06 g); m.p. 163.8-165.2° C.; TLC: R$_f$=0.42 (DCM:MeOH (9:0.2; v/v)); C$_{22}$H$_{21}$Cl$_2$N$_3$O$_3$ (446.33), Monoisotopic mass: 446.10. UPLC (99% purity): t$_R$=7.59 min, (M+H)$^+$ 446.1. $^1$H NMR (500 MHz, CDCl$_3$) δ 2.63-2.78 (m, 5H), 2.98-3.13 (m, 2H), 3.20-3.36 (m, 3H), 3.59-3.68 (m, 1H), 3.97-4.00 (m, 1H), 6.09 (s, 1H), 6.64 (d, J=1.7 Hz, 2H), 6.80 (t, J=1.7 Hz, 1H), 7.33-7.38 (m, 3H), 7.42 (d, J=6.7 Hz, 2H). $^{13}$C NMR (126 MHz, CDCl$_3$) δ 28.1, 42.2, 45.4, 48.0, 48.2, 56.9, 114.4, 119.8, 128.8, 129.1, 129.9, 132.9, 135.6, 152.1, 165.2, 176.4.

Example 5. 1-(2-Oxo-1-phenyl-2-(4-(m-tolyl)piperazin-1-yl)ethyl)pyrrolidine-2,5-dione The compound was prepared according to procedure described in Example 2. 2-(2,5-Dioxopyrrolidin-1-yl)-2-phenylacetic acid (1.40 g, 6 mmol, 1 eq) and 1-(3-methylphenyl)piperazine (1.18 g, 6 mmol, 1 eq) were used as starting materials. The crude product was purified by column chromatography using DCM:MeOH (9:0.3; v/v) eluent system.

White solid. Yield: 86% (2.02 g); m.p. 188.7-192.1° C.; TLC: R$_f$=0.45 (DCM:MeOH (9:0.3; v/v)); C$_{23}$H$_{25}$N$_3$O$_3$ (391.47), Monoisotopic mass: 391.19. UPLC (98.9% purity): t$_R$=6.35 min, (M+H)$^+$ 392.2. $^1$H NMR (300 MHz, CDCl$_3$) δ 2.36 (s, 3H), 2.57-2.78 (m, 5H), 2.91-3.54 (m, 3H), 3.63-4.55 (m, 4H), 6.06 (s, 1H), 7.22 (d, 1H, J=7.5 Hz), 7.27-7.62 (m, 8H); $^{13}$C NMR (75 MHz, CDCl$_3$) δ 21.4, 28.1, 39.7, 43.0, 54.1, 54.6, 56.5, 117.9, 121.7, 128.9, 129.3, 129.7, 130.2, 130.8, 132.3, 141.0, 141.8, 165.4, 176.3.

Example 6. 1-(2-Oxo-1-phenyl-2-(4-(3-(trifluoromethyl)phenyl)piperazin-1-yl)ethyl)pyrrolidine-2,5-dione The compound was prepared according to procedure described in Example 2. 2-(2,5-Dioxopyrrolidin-1-yl)-2-phenylacetic acid (1.40 g, 6 mmol, 1 eq) and 1-[3-(trifluoromethyl)phenyl]piperazine (1.38 g, 6 mmol, 1 eq) were used as starting materials. The crude product was purified by column chromatography using DCM:MeOH (9:0.2; v/v) eluent system.

White solid. Yield: 82% (2.19 g); m.p. 150.3-151.4° C.; TLC: R$_f$=0.34 (DCM:MeOH (9:0.2; v/v)); C$_{23}$H$_{22}$F$_3$N$_3$O$_3$ (445.44), Monoisotopic mass: 445.16. UPLC (100% purity): t$_R$=6.94 min, (M+H)$^+$ 446.2. $^1$H NMR (300 MHz, CDCl$_3$) δ 2.60-2.86 (m, 5H), 3.00-3.20 (m, 2H), 3.23-3.44 (m, 3H), 3.62-3.76 (m, 1H), 3.93-4.06 (m, 1H), 6.12 (s, 1H), 6.94-7.04 (m, 2H), 7.09 (d, 1H, J=7.7 Hz), 7.28-7.51 (m, 6H); $^{13}$C NMR (75 MHz, CDCl$_3$) δ 28.0, 42.2, 45.6, 48.4, 48.6, 56.8, 112.7 (q, J=4.6 Hz), 116.7 (q, J=4.6 Hz), 119.2, 123.4 (q, J=271.8 Hz), 128.7, 128.9, 129.7, 129.8, 131.5 (q, J=31.8 Hz), 132.9, 150.8, 165.1, 176.3.

Example 7. 1-(2-Oxo-1-phenyl-2-(4-(4-(trifluoromethyl)phenyl)piperazin-1-yl)ethyl)pyrrolidine-2,5-dione The compound was prepared according to procedure described in Example 2. 2-(2,5-Dioxopyrrolidin-1-yl)-2-phenylacetic acid (1.40 g, 6 mmol, 1 eq) and 1-[4-(trifluoromethyl)phenyl]piperazine (1.38 g, 6 mmol, 1 eq) were used as starting materials. The crude product was purified by column chromatography using DCM:MeOH (9:0.3; v/v) eluent system.

White solid. Yield: 62% (1.66 g); m.p. 173.2-174.3° C.; TLC: $R_f$=0.49 (DCM:MeOH (9:0.3; v/v)); $C_{23}H_{22}F_3N_3O_3$ (445.44), Monoisotopic mass: 445.16. UPLC (100% purity): $t_R$=6.89 min, (M+H)$^+$ 446.2. $^1$H NMR (300 MHz, CDCl$_3$) δ 2.61-2.85 (m, 5H), 3.04-3.43 (m, 5H), 3.63-3.77 (m, 1H), 3.91-4.05 (m, 1H), 6.12 (s, 1H), 6.83 (d, 2H, J=8.6 Hz), 7.30-7.40 (m, 3H), 7.40-7.50 (m, 4H); $^{13}$C NMR (75 MHz, CDCl$_3$) δ 28.0, 42.1, 45.4, 47.6, 47.9, 56.8, 115.0, 124.5 (q, J=270.6 Hz), 126.5 (q, J=4.6 Hz), 128.7, 128.8, 128.9, 129.8, 132.8, 152.7, 165.1, 176.3.

Example 8. 1-(2-(4-(3,5-Bis(trifluoromethyl)phenyl)piperazin-1-yl)-2-oxo-1-phenylethyl)pyrrolidine-2,5-dione The compound was prepared according to procedure described in Example 2. 2-(2,5-Dioxopyrrolidin-1-yl)-2-phenylacetic acid (1.40 g, 6 mmol, 1 eq) and 1-[3,5-bis(trifluoromethyl)phenyl]piperazine (1.18 g, 6 mmol, 1 eq) were used as starting materials. The crude product was purified by column chromatography using DCM:MeOH (9:0.5; v/v) eluent system.

White solid. Yield: 69% (2.12 g); m.p. 228.1-229.4° C.; TLC: $R_f$=0.47 (DCM:MeOH (9:0.5; v/v)); $C_{24}H_{21}F_6N_3O_3$ (513.44), Monoisotopic mass: 513.13. UPLC (100% purity): $t_R$=6.58 min, (M+H)$^+$ 514.1. $^1$H NMR (300 MHz, CDCl$_3$) δ 2.52-2.75 (m, 4H), 2.82-3.07 (m, 4H), 3.12-3.86 (m, 4H), 6.11 (s, 1H), 6.97-7.05 (m, 3H), 7.22-7.61 (m, 5H).

Example 9. 1-(2-Oxo-1-phenyl-2-(4-(3-(difluoromethyl)phenyl)piperazin-1-yl)ethyl)pyrrolidine-2,5-dione The compound was prepared according to procedure described in Example 2. 2-(2,5-Dioxopyrrolidin-1-yl)-2-phenylacetic acid (1.40 g, 6 mmol, 1 eq) and 1-(3-difluoromethylphenyl)piperazine (1.27 g, 6 mmol, 1 eq) were used as starting materials. The crude product was purified by column chromatography using DCM:MeOH (9:0.2; v/v) eluent system.

White solid. Yield: 83% (2.13 g); m.p. 156.4-157.6° C.; TLC: $R_f$=0.55 (DCM:MeOH (9:0.2; v/v)); $C_{23}H_{23}F_2N_3O_3$ (427.45), Monoisotopic mass: 427.17. UPLC (100% purity): $t_R$=6.36 min, (M+H)$^+$ 428.2. $^1$H NMR (300 MHz, CDCl$_3$) δ 2.58-2.78 (m, 5H), 3.02-3.18 (m, 2H), 3.24-3.46 (m, 3H), 3.62-4.08 (m, 2H), 6.12 (s, 1H), 6.44-7.62 (m, 1H), 6.94-7.04 (m, 2H), 7.28-7.51 (m, 7H).

Example 10. 1-(2-Oxo-1-phenyl-2-(4-(3-(trifluoromethoxy)phenyl)piperazin-1-yl)ethyl)pyrrolidine-2,5-dione The compound was prepared according to procedure described in Example 2. 2-(2,5-Dioxopyrrolidin-1-yl)-2-phenylacetic acid (1.40 g, 6 mmol, 1 eq) and 1-[3-(trifluoromethoxy)phenyl]piperazine (1.48 g, 6 mmol, 1 eq) were used as starting materials. The crude product was purified by column chromatography using DCM:MeOH (9:0.3; v/v) eluent system.

White solid. Yield: 89% (2.46 g); m.p. 100.3-101.6° C.; TLC: $R_f$=0.42 (DCM:MeOH (9:0.3; v/v)); $C_{23}H_{22}F_3N_3O_4$ (461.44), Monoisotopic mass: 461.16. UPLC (100% purity): $t_R$=7.15 min, (M+H)$^+$ 462.2. $^1$H NMR (300 MHz, CDCl$_3$) δ 2.63-2.79 (m, 5H), 3.00-3.16 (m, 2H), 3.22-3.39 (m, 3H), 3.93-4.05 (m, 1H), 3.63-3.75 (m, 1H), 6.12 (s, 1H), 6.62 (s, 1H), 6.66-6.78 (m, 2H), 7.16-7.28 (m, 1H), 7.32-7.48 (m, 5H); $^{13}$C NMR (75 MHz, CDCl$_3$) δ 28.0, 42.2, 45.5, 48.3, 48.5, 56.8, 108.8, 112.1, 114.2, 120.4 (q, J=256.8 Hz), 128.7, 128.9, 129.8, 130.2, 132.8, 150.2, 151.9, 165.1, 176.3.

Example 11. 1-(2-Oxo-1-phenyl-2-(4-(4-(trifluoromethoxy)phenyl)piperazin-1-yl)ethyl)pyrrolidine-2,5-dione The compound was prepared according to procedure described in Example 2. 2-(2,5-Dioxopyrrolidin-1-yl)-2-phenylacetic acid (1.40 g, 6 mmol, 1 eq) and 1-[4-(trifluoromethoxy)phenyl]piperazine (1.48 g, 6 mmol, 1 eq) were used as starting materials. The crude product was purified by column chromatography using DCM:MeOH (9:0.3; v/v) eluent system.

White solid. Yield: 83% (2.29 g); m.p. 102.3-103.5° C.; TLC: $R_f$=0.43 (DCM:MeOH (9:0.3; v/v)); $C_{23}H_{22}F_3N_3O_4$ (461.44), Monoisotopic mass: 461.16. UPLC (100% purity): $t_R$=7.17 min, (M+H)$^+$ 462.2. $^1$H NMR (300 MHz, CDCl$_3$) δ 2.61-2.73 (m, 5H), 2.98-3.13 (m, 2H), 3.20-3.37 (m, 3H), 3.91-4.08 (m, 1H), 3.63-3.75 (m, 1H), 6.13 (s, 1H), 6.60 (s, 1H), 6.63-6.79 (m, 2H), 7.14-7.28 (m, 1H), 7.29-7.51 (m, 5H).

Example 12. 1-(2-Oxo-1-phenyl-2-(4-(3-(trifluoromethyl(sulfanyl)phenyl)piperazin-1-yl)ethyl)pyrrolidine-2,5-dione The compound was prepared according to procedure described in Example 2. 2-(2,5-Dioxopyrrolidin-1-yl)-2-phenylacetic acid (1.40 g, 6 mmol, 1 eq) and 1-[3-(trifluoromethylthio)phenyl]piperazine (1.57 g, 6 mmol, 1 eq) were used as starting materials. The crude product was purified by column chromatography using DCM:MeOH (9:0.5; v/v) eluent system.

White solid. Yield: 64% (1.83 g); m.p. 97.8-99.2° C.; TLC: $R_f$=0.48 (DCM:MeOH (9:0.5; v/v)); $C_{23}H_{22}F_3N_3O_3S$ (477.50), Monoisotopic mass: 478.13. UPLC (99% purity): $t_R$=7.55 min, (M+H)$^+$478.1. $^1$H NMR (500 MHz, CDCl$_3$) δ 2.64-2.78 (m, 5H), 3.01-3.07 (m, 1H), 3.09-3.15 (m, 1H), 3.24-3.32 (m, 2H), 3.34 (dd, J=7.7, 3.2 Hz, 1H), 3.62-3.75 (m, 1H), 3.99 (ddd, J=13.2, 5.7, 3.4 Hz, 1H), 6.11 (s, 1H), 6.92 (dd, J=8.0, 2.3 Hz, 1H), 7.06 (s, 1H), 7.12 (d, J=7.4 Hz, 1H), 7.24-7.29 (m, 1H), 7.33-7.38 (m, 3H), 7.43 (d, J=6.8 Hz, 2H). $^{13}$C NMR (126 MHz, CDCl$_3$) δ 28.1, 45.6, 48.4, 48.7, 56.9, 118.5, 123.7, 125.3, 127.8, 128.5, 129.4 (d, J=141.2 Hz), 129.6 (d, J=137.0 Hz), 130.9, 132.9, 151.4, 165.2, 176.4.

Example 13. 1-(2-(4-([1,1'-Biphenyl]-3-yl)piperazin-1-yl)-2-oxo-1-phenylethyl)pyrrolidine-2,5-dione The compound was prepared according to procedure described in Example 2. 2-(2,5-Dioxopyrrolidin-1-yl)-2- phenylacetic acid (1.40 g, 6 mmol, 1 eq) and 1-(biphen-3-yl)piperazine (1.43 g, 6 mmol, 1 eq) were used as starting materials. The crude product was purified by column chromatography using DCM:MeOH (9:0.5; v/v) eluent system.

White solid. Yield: 82% (2.23 g); m.p. 114.1-115.4° C.; TLC: $R_f$=0.4 (DCM:MeOH (9:0.5; v/v)); $C_{28}H_{27}N_3O_3$ (453.54) Monoisotopic mass: 453.20. UPLC (100% purity): $t_R$=7.43 min, (M+H)$^+$454.2. $^1$H NMR (300 MHz, CDCl$_3$) δ 2.56-2.81 (m, 5H), 3.00-3.21 (m, 2H), 3.23-3.56 (m, 3H), 3.65-3.79 (m, 1H), 3.94-4.11 (m, 1H), 6.14 (s, 1H), 6.83 (dd, 1H, J=8.1, 2.0 Hz), 7.00-7.17 (m, 2H), 7.27-7.62 (m, 11H); $^{13}$C NMR (75 MHz, CDCl$_3$) δ 28.1, 42.5, 45.8, 49.0, 49.2, 56.8, 115.4, 115.6, 119.7, 127.2, 127.4, 128.7, 128.8, 129.6, 129.9, 132.9, 141.4, 142.5, 151.1, 165.0, 176.4.

Example 14. 1-(1-(4-Fluorophenyl)-2-oxo-2-(4-(3-(trifluoromethyl)phenyl)piperazin-1-yl)ethyl)pyrrolidine-2,5-dione The compound was prepared according to procedure described in Example 2. 2-(2,5-Dioxopyrrolidin-1-yl)-2-(4-fluorophenyl)acetic acid (1.51 g, 6 mmol, 1 eq) and 1-[3-(trifluoromethoxy)phenyl]piperazine (1.38 g, 6 mmol, 1 eq) were used as starting materials. The crude product was purified by column chromatography using DCM:MeOH (9:0.5; v/v) eluent system.

White solid. Yield: 73% (2.03 g); m.p. 88.8-90.7° C.; TLC: $R_f$=0.63 (DCM:MeOH (9:0.5; v/v)); $C_{23}H_{21}F_4N_3O_3$ (463.43), Monoisotopic mass: 463.15. UPLC (100% purity): $t_R$=7.05 min, (M+H)$^+$464.2. $^1$H NMR (300 MHz, CDCl$_3$) δ 2.61-2.89 (m, 5H), 3.02-3.46 (m, 5H), 3.67-3.80 (m, 1H), 3.88-4.04 (m, 1H), 6.09 (s, 1H), 6.94-7.27 (m, 6H), 7.29-7.40 (m, 2H). $^{13}$C NMR (75 MHz, CDCl$_3$) δ 28.0, 42.3, 45.6, 48.5, 48.6, 56.0, 112.7 (q, J=3.4 Hz), 115.9, 116.2, 116.7 (q, J=3.4 Hz), 117.0, 119.3, 124.1 (q, J=272.9 Hz), 125.5 (d, J=3.4 Hz), 129.7, 130.2, 130.3, 131.5 (q, J=31.1 Hz), 135.1 (d, J=6.9 Hz), 150.7, 160.9, 164.2, 164.5, 176.23.

Example 15. 1-(2-(4-(Naphth-2-yl)piperazin-1-yl)-2-oxo-1-phenylethyl)pyrrolidine-2,5-dione The compound was prepared according to procedure described in Example 2. 2-(2,5-Dioxopyrrolidin-1-yl)-2-phenylacetic acid (1.40 g, 6 mmol, 1 eq) and 1-(naphth-2-yl)piperazine (1.27 g, 6 mmol, 1 eq) were used as starting materials. The crude product was purified by column chromatography using DCM:MeOH (9:0.5; v/v) eluent system.

White solid. Yield: 79% (2.02 g); m.p. 197.1-198.5° C.; TLC: $R_f$=0.71 ((DCM:MeOH (9:0.5; v/v)); $C_{26}H_{25}N_3O_3$ (427.50), Monoisotopic mass: 427.19. UPLC (100% purity): $t_R$=6.97 min (M+H)$^+$ 428.2. $^1$H NMR (300 MHz, CDCl$_3$) δ 2.58-2.87 (m, 5H), 3.03-3.25 (m, 2H), 3.29-3.60 (m, 3H), 3.69-3.89 (m, 1H), 3.96-4.17 (m, 1H), 6.12-6.18 (m, 1H), 7.00-7.24 (m, 2H), 7.28-7.54 (m, 7H), 7.61-7.80 (m, 3H).

Example 16. 1-(2-(4-(Benzo[b]thiophen-5-yl)piperazin-1-yl)-2-oxo-1-phenylethyl)pyrrolidine-2,5-dione The compound was prepared according to procedure described in Example 2. 2-(2,5-Dioxopyrrolidin-1-yl)-2-phenylacetic acid (1.40 g, 6 mmol, 1 eq) and 1-(benzo[b]thiophen-5-yl)piperazine (1.30 g, 6 mmol, 1 eq) were used as starting materials. The crude product was purified by column chromatography using DCM:MeOH (9:0.5; v/v) eluent system.

White solid. Yield: 79% (2.05 g); m.p. 164.1-165.3° C.; TLC: $R_f$=0.66 ((DCM:MeOH (9:0.5; v/v)); $C_{24}H_{23}N_3O_3S$ (433.53), Monoisotopic mass: 433.15 UPLC (100% purity): $t_R$=6.62 min, (M+H)$^+$ 434.1. $^1$H NMR (300 MHz, CDCl$_3$) δ 2.56-2.85 (m, 5H), 2.96-3.17 (m, 2H), 3.20-3.54 (m, 3H), 3.66-3.87 (m, 1H), 3.96-4.12 (m, 1H), 6.14 (s, 1H), 6.99 (dd, J=8.7, 1.9 Hz, 1H), 7.15-7.25 (m, 1H), 7.30-7.55 (m, 7H), 7.72 (d, J=8.8 Hz, 1H).

Example 17. 1-(2-(4-(1,2-Benzoxazol-5-il)piperazin-1-yl)-2-oxo-1-phenylethyl)pyrrolidine-2,5-dione The compound was prepared according to procedure described in Example 2. 2-(2,5-Dioxopyrrolidin-1-yl)-2-phenylacetic acid (1.40 g, 6 mmol, 1 eq) and 5-(piperazin-1-yl)benzo[d]isoxazole (1.22 g, 6 mmol, 1 eq) were used as starting materials. The crude product was purified by column chromatography using DCM:MeOH (9:0.5; v/v) eluent system.

White solid. Yield: 57% (1.43 g); m.p. 186.4-187.8° C.; TLC: $R_f$=0.58 (DCM:MeOH (9:0.5; v/v)); $C_{23}H_{22}N_4O_4$ (418.45), Monoisotopic mass: 418.16. UPLC (98% purity): $t_R$=7.25 min, (M+H)$^+$419.1. $^1$H NMR (300 MHz, CDCl$_3$) δ 2.57-2.86 (m, 5H), 2.95-3.19 (m, 3H), 3.22-3.53 (m, 2H), 3.62-3.84 (m, 2H), 3.94-4.11 (m, 1H), 6.14 (s, 1H), 7.05-7.32 (m, 1H), 7.29-7.54 (m, 6H), 7.98 (d, J=8.8 Hz, 1H).

Example 18. 1-(2-(4-(3-Chlorophenyl)piperidin-1-yl)-2-oxo-1-phenylethyl)pyrrolidine-2,5-dione The compound was prepared according to procedure described in Example 2. 2-(2,5-Dioxopyrrolidin-1-yl)-2-phenylacetic acid (1.40 g, 6 mmol, 1 eq) and 4-(3-chlorophenyl)piperidine (1.17 g, 6 mmol, 1 eq) were used as starting materials. The crude product was purified by column chromatography using DCM:MeOH (9:0.5; v/v) eluent system.

White solid. Yield: 74% (1.83 g); m.p. 111.8-113.4° C.; TLC: $R_f$=0.43 (DCM:MeOH (9:0.5; v/v)); $C_{23}H_{23}ClN_2O_3$ (410.90), Monoisotopic mass: 410.14. UPLC (100% purity): $t_R$=7.05 min, (M+H)$^+$411.1, $^1$H NMR (300 MHz, CDCl$_3$) δ 1.52-2.05 (m, 4H), 2.33-2.84 (m, 8H), 2.96-3.34 (m, 1H), 6.15 (s, 1H), 7.05-7.28 (m, 6H), 7.32-7.66 (m, 3H).

Example 19. 1-(2-Oxo-1-phenyl-2-(4-(3-(trifluoromethyl)phenyl)piperidin-1-yl)ethyl)pyrrolidine-2,5-dione The compound was prepared according to procedure described in Example 2. 2-(2,5-Dioxopyrrolidin-1-yl)-2-phenylacetic acid (1.40 g, 6 mmol, 1 eq) and 1-[3-(trifluoromethyl)phenyl]piperidine (1.37 g, 6 mmol, 1 eq) were used as starting materials. The crude product was purified by column chromatography using DCM:MeOH (9:0.5; v/v) eluent system.

White solid. Yield: 85% (2.26 g); m.p. 100.1-101.5° C.; TLC: $R_f$=0.45 (DCM:MeOH (9:0.5; v/v)); $C_{24}H_{23}F_3N_2O_3$ (444.45), Monoisotopic mass: 444.17. UPLC (100% purity): $t_R$=7.26 min, (M+H)$^+$ 445.1. $^1$H NMR (300 MHz, CDCl$_3$) δ 1.49-2.00 (m, 3H), 2.54-2.83 (m, 8H), 2.94-3.77 (m, 2H), 6.14 (s, 1H), 7.09-7.60 (m, 9H).

Example 20. 1-(2-Oxo-1-phenyl-2-(4-(3-(trifluoromethoxy)phenyl)piperidin-1-yl)ethyl)pyrrolidine-2,5-dione The compound was prepared according to procedure described in Example 2. 2-(2,5-Dioxopyrrolidin-1-yl)-2- phenylacetic acid (1.40 g, 6 mmol, 1 eq) and 4-[3-(trifluoromethoxy)phenyl]piperidine (1.45 g, 6 mmol, 1 eq) were used as starting materials. The crude product was purified by column chromatography using DCM:MeOH (9:0.5; v/v) eluent system.

White solid. Yield: 79% (2.18 g); m.p. 112.1-113.2° C.; TLC: $R_f$=0.47 (DCM:MeOH (9:0.5; v/v)); $C_{24}H_{23}F_3N_2O_4$ (460.45), Monoisotopic mass: 460.16. UPLC (100% purity): $t_R$=7.12 min, (M+H)$^+$461.1, $^1$H NMR (300 MHz, CDCl$_3$) δ 1.38-2.15 (m, 3H), 2.49-2.92 (m, 8H), 2.99-3.85 (m, 2H), 6.15 (s, 1H), 7.11-7.64 (m, 9H).

Example 21. 1-(1-Oxo-3-phenyl-1-(4-phenylpiperazin-1-yl)prop-2-yl)pyrrolidine-2,5-dione The compound was prepared according to procedure described in Example 2. 2-(2,5-Dioxopyrrolidin-1-yl)-3-phenylpropanoic acid (1.48 g, 6 mmol, 1 eq) and 1-phenylpiperazine (0, 97 g, 6 mmol, 1 eq) were used as starting materials. The crude product was purified by column chromatography using DCM:MeOH (9:0.5; v/v) eluent system.

White solid. Yield: 87% (1.13 g); m.p. 121.7-123.2° C.; TLC: $R_f$=0.62 (DCM:MeOH (9:0.5; v/v)); $C_{23}H_{25}N_3O_3$ (391.47), Monoisotopic mass: 392.19. UPLC (100% purity): $t_R$=6.22 min, (M+H)$^+$ 392.1. $^1$H NMR (300 MHz, CDCl$_3$) δ 2.49-2.61 (m, 4H), 3.08 (d, J=16.4 Hz, 4H), 3.31-3.89 (m, 6H), 5.19 (dd, J=10.3, 6.1 Hz, 1H), 6.83-6.96 (m, 3H), 7.13-7.33 (m, 7H). $^{13}$C NMR (75 MHz, CDCl$_3$) δ 27.8, 34.2, 42.5, 45.4, 49.3, 49.6, 52.9, 116.6, 120.7, 127.1, 128.6, 129.1, 129.3, 136.7, 150.7, 166.4, 176.5.

Example 22. 1-(1-(4-(3-Chlorophenyl)piperazin-1-yl)-1-oxo-3-phenylpropan-2-yl)pyrrolidine-2,5-dione The compound was prepared according to procedure described in Example 2. 2-(2,5-Dioxopyrrolidin-1-yl)-3-phenylpropanoic acid (1.48 g, 6 mmol, 1 eq) and 1-(3-chlorophenyl)piperazine (1.40 g, 6 mmol, 1 eq) were used as starting materials. The crude product was purified by column chromatography using DCM:MeOH (9:0.5; v/v) eluent system.

White solid. Yield: 87% (1.23 g); m.p. 114.3-116.2° C.; TLC: $R_f$=0.80 (DCM:MeOH (9:0.5; v/v)); $C_{23}H_{24}ClN_3O_3$ (425.91), Monoisotopic mass: 426.15. UPLC (100% purity): $t_R$=6.97 min, (M+H)$^+$426.1. $^1$H NMR (300 MHz, CDCl$_3$) δ 2.49-2.64 (m, 4H), 3.07 (d, J=15.3 Hz, 4H), 3.30-3.86 (m, 6H), 5.17 (dd, J=10.1, 6.2 Hz, 1H), 6.73 (ddd, J=8.3, 2.2, 0.9 Hz, 1H), 6.79-6.88 (m, 2H), 7.06-7.35 (m, 6H). $^{13}$C NMR (75 MHz, CDCl$_3$) δ 27.8, 34.2, 42.2, 45.2, 48.7, 49.0, 52, 9, 114.4, 116.3, 120.2, 127.1, 128.6, 129.1, 130.2, 135.0, 136.6, 151.7, 166.4, 176.5.

Example 23. 1-(1-Oxo-3-phenyl-1-(4-(3-(trifluoromethyl)phenyl)piperazin-1-yl)propan-2-yl)pyrrolidine-2,5-dione The compound was prepared according to procedure described in Example 2. 2-(2,5-Dioxopyrrolidin-1-yl)-3-phenylpropanoic acid (1.48 g, 6 mmol, 1 eq) and 1-[3-(trifluoromethyl)phenyl]piperazine (1.38 g, 6 mmol, 1 eq) were used as starting materials. The crude product was purified by column chromatography using DCM:MeOH (9:0.5; v/v) eluent system.

White solid. Yield: 84% (1.59 g); m.p. 126.1-127.2° C.; TLC: $R_f$=0.72 (DCM:MeOH (9:0.5; v/v)); $C_{24}H_{24}F_3N_3O_3$ (459.47), Monoisotopic mass: 460.18. UPLC (100% purity): $t_R$=7.22 min, (M+H)$^+$460.1. 1H NMR (300 MHz, CDCl3) δ 2.50-2.64 (m, 4H) 3.12 (d, J=14.8 Hz, 4H), 3.32-3.89 (m, 6H) 5.18 (dd, J=9.9, 6.2 Hz, 1H), 6.94-7.42 (m, 9H).

Example 24. 1-(1-(4-([1,1'-Biphenyl]-3-yl)piperazin-1-yl)-1-oxo-3-phenylpropan-2-yl)pyrrolidine-2, 5-dione The compound was prepared according to procedure described in Example 2. 2-(2,5-Dioxopyrrolidin-1-yl)-3-phenylpropanoic acid (1.48 g, 6 mmol, 1 eq) and 1-(biphenyl-3)piperazine (1.43 g, 6 mmol, 1 eq) were used as starting materials. The crude product was purified by column chromatography using DCM:MeOH (9:0.5; v/v) eluent system.

White solid. Yield: 88% (1.46 g); m.p. 119.1-120.0° C.; TLC: $R_f$=0.77 (DCM:MeOH (9:0.5; v/v)); $C_{29}H_{29}N_3O_3$ (467.57), Monoisotopic mass: 467.22. UPLC (100% purity): $t_R$=7.63 min, (M+H)$^+$ 468.2. $^1$H NMR (300 MHz, CDCl$_3$) δ 2.50-2.63 (m, 4H) 3.16 (d, J=18.9 Hz, 4H), 3.32-3.91 (m, 6H), 5.20 (dd, J=10.2, 6.0 Hz, 1H) 6.88 (dd, J=8.1, 1.8 Hz, 1H), 7.06-7.38 (m, 9H), 7.39-7.48 (m, 2H), 7.51-7.62 (m, 2H). $^{13}$C NMR (75 MHz, CDCl$_3$) δ 27.8, 34.2, 42.5, 45.4, 49.4, 49.7, 53.0, 115.5, 115.7, 119.7, 127.1, 127.2, 127.4, 128.6, 128.7, 129.1, 129.6, 136.7, 141.4, 142.5, 151.1, 166.4, 176.5.

Example 25. 1-(1-Oxo-3-phenyl-1-(4-(3-(trifluoromethoxy)phenyl)piperazin-1-yl)propan-2-yl)pyrrolidine-2,5-dione The compound was prepared according to procedure described in Example 2. 2-(2,5-Dioxopyrrolidin-1-yl)-3-phenylpropanoic acid (1.48 g, 6 mmol, 1 eq) and 1-[3-(trifluoromethoxy)phenyl]piperazine (1.48 g, 6 mmol, 1 eq) were used as starting materials. The crude product was purified by column chromatography using DCM:MeOH (9:0.5; v/v) eluent system.

White solid. Yield: 83% (1.32 g); m.p. 104.4-105.5° C.; TLC: $R_f$=0.71 (DCM:MeOH (9:0.5; v/v)); $C_{24}H_{24}F_3N_3O_4$ (475.47), Monoisotopic mass: 475.17. UPLC (100% purity): $t_R$=7.40 min, (M+H)$^+$ 476.1. $^1$H NMR (300 MHz, CDCl$_3$) δ 2.50-2.63 (m, 4H, 3.10 (d, J=16.4 Hz, 4H), 3.31-3.86 (m, 6H), 5.18 (dd, J=9.9, 6.2 Hz, 1H), 6.62-6.85 (m, 3H), 7.11-7.36 (m, 6H).

Example 26. Determination of In Vivo Anticonvulsant Activity in Mice

The male Swiss albino mice (CD-1) weighing 18-26 g were used. All procedures were carried out in accordance with applicable Polish and international guidelines on the ethics of animal testing, after obtaining appropriate institutional approval. The substances were administered intraperitoneally (i.p.), in 1% aqueous solution of Tween, as single injections with a volume of 10 ml/kg, 30 minutes before the given test. Screening was performed on groups consisted of 4 mice. The average effective dose (ED$_{50}$) in given test and toxic dose in the rotarod test (TD$_{50}$) was estimated based on the results obtained in 3-4 groups of animals consisting of 6 mice. All tests were carried out based on the procedures described in the specialist literature.

Example 27. Maximal Electroshock Seizure Test (MES)

In the MES test, the seizures were induced by an electrical stimulus lasting of 0.2 s duration, 500 V voltage and 25 mA intensity. The electrical stimuli was generated using an electric shock generator (Rodent shocker, Type 221, Hugo Sachs Elektronik, Germany) and delivered to the animal using electrodes placed on the auricles. The study was conducted 30 minutes after intraperitoneal administration of the compounds at various doses. During the experiment, the number of animals that experienced a seizure episode in the form of tonic extension of the hind limbs was counted (Kamiński, K.; Rapacz, A.; Łuszczki, J. J.; Latacz, G.; Obniska, J.; Kieć-Kononowicz, K.; Filipek, B. *Bioorg. Med. Chem.* 2015, 23, 2548-2561; Castel-Branco, M. M.; Alves, G. L.; Figueiredo, I. V.; Falcão, A. C.; Caramona, M. M. *Methods Find. Exp. Clin. Pharmacol.* 2009, 31, 101-106).

Example 28. Psychomotor Seizure Test (6 Hz Test)

In the 6 Hz test, seizures were induced by an electric stimulus of 32 mA and/or 44 mA and a frequency of 6 pulses per second. An electrical pulse was generated using an electric shock generator (ECT Unit 57800; Ugo Basile, Gemonio, Italy) and delivered to the animal using ocular electrodes. Before starting the test, the eye surface was gently moistened with a solution of local anesthetic (1% lidocaine solution). The study was conducted 30 minutes after intraperitoneal administration of the compounds at various doses. An electrical pulse was delivered continuously for a period of 3 seconds, followed by observation of the animal for a period of 10 seconds. During this time, immobility or stun associated with rearing, forelimb clonus, twitching of the vibrissae and Straub's tail were observed. These symptoms persist throughout the observation period, indicating the occurrence of psychomotor seizures in mice. Mice resuming normal behavior within 10 s after stimulation were considered as protected (Barton, M. E.; Klein, B. D.; Wolf, H. H.; White, H. S. *Epilepsy Res.* 2001, 47, 217-227; Wojda, E.; Wlaź, A.; Patsalos, P. N.; Łuszczki, J. J. *Epilepsy Res.* 2009, 86, 163-174).

Example 29. Subcutaneous Pentylenetetrazole Seizure Test (scPTZ)

In the scPTZ test, seizures were induced by subcutaneous administration of pentylenetetrazole (PTZ) at a dose of 100 mg/kg. This caused clonic seizures with accompanying loss of the righting reflex. Test compounds were administered 30 minutes before the experiment. After PTZ administration, the animals were placed individually in transparent containers and observed for a period of 30 minutes for the occurrence of clonic seizures. During this time, the latency of the first onset of clonic seizures, defined as clonus of the whole body lasting at least 3 seconds with loss of the righting reflex and the number of seizure episodes during the test were noted and compared with control group. The absence of clonic convulsions within the observed time period was interpreted as the compound's ability to protect against PTZ-induced seizures (Ferreri, G.; Chimirri, A.; Russo, E.; Gitto, R.; Gareri, P.; De Sarro, A.; De Sarro, G. *Pharmacol. Biochem. Behav.* 2004, 77, 85-94; Łączkowski, K.; Sałat, K.; Misiura, K.; Podkowa, A.; Malikowska, N. *J. Enzyme Inhib. Med. Chem.* 2016, 31, 1576-82).

Example 30. Influence on Mouse Motor Coordination in the Rotarod Test

The influence of tested compounds on motor coordination was assessed in the rotarod test (the apparatus used—May Commat, RR 0711 Rota Rod, Turkey). Mice were trained the day before the actual experiment. They were placed individually on a 2 cm diameter rod rotating at 10 revolutions per minute (rpm). During each training session, the animals remained on the rod for 3 minutes. The experiment was carried out 30 minutes after administration of the compounds. Motor coordination was tested at the speed of the rotating bar: 10 rpm during 60 seconds. Motor impairments were defined as the inability to remain on the rotating rod for 1 min. The mean time spent on the rod was counted in each experimental group (Dunham, N. W.; Miya, T. A.; Edwards, L. D. *J. Am. Pharm. Assoc.* 1957, 46, 64-66, Łączkowski, K.; Sałat, K.; Misiura, K.; Podkowa, A.; Malikowska, N. *J. Enzyme Inhib. Med. Chem.* 2016, 31, 1576-82).

Example 31. Statistical Analysis

The $ED_{50}$ (effective dose) and $TD_{50}$ (toxic dose) values along with the corresponding 95% confidence intervals were calculated based on the Litchfield and Wilcoxon method (Litchfield, J. T., Wilcoxon, F., 1949. A simplified method of evaluating dose-effect experiments. J. Pharmacol. Exp. Ther. 96, 99-113). To perform a statistical evaluation of the results, one-way ANOVA variance analysis and Dunnett's post hoc test (multiple comparison test) were used. The value at the significance level $p<0.05$ was considered statistically significant.

Example 32. Results of Anticonvulsant Activity Studies

The compounds of the invention showed broad anticonvulsant activity by acting effectively in the MES test, 6 Hz (32 mA and/or 44 mA) and scPTZ at a dose of 100 mg/kg. At time point of 30 min. they protected from 50-100% of the animals tested. The most potent protection revealed compounds containing electron withdrawing substituents at position 3 of the aromatic ring connected to piperazine moiety, preferably Cl, $CF_3$, $OCF_3$, $SCF_3$, $CHF_2$ or phenyl substituent, for which k is preferably 0. Table 1 shows pharmacological screening data for selected substances.

TABLE 1

Data from screening studies at a dose of 100 mg/kg for selected compounds according to the general formula (II).

| Com- | Test* | | | |
|---|---|---|---|---|
| pound | MES | 6 Hz (32 mA) | 6 Hz (44 mA) | ScPTZ |
| 2 | 4/4 | 3/4 | 2/4 | 3/4 |
| 3 | 4/4 | 4/4 | 3/4 | 3/4 |
| 4 | 3/4 | 4/4 | — | 3/4 |
| 5 | 3/4 | 4/4 | 2/4 | 3/4 |
| 6 | 4/4 | 4/4 | 4/4 | 4/4 |
| 7 | 3/4 | 3/4 | — | 3/4 |
| 8 | 4/4 | 3/4 | — | 4/4 |
| 19 | 4/4 | 4/4 | 2/4 | 4/4 |
| 10 | 4/4 | 4/4 | 3/4 | 2/4 |
| 11 | 3/4 | 3/4 | — | 2/4 |
| 12 | 4/4 | 4/4 | 3/4 | 4/4 |
| 13 | 4/4 | 4/4 | 4/4 | 2/4 |
| 14 | 4/4 | 3/4 | — | 2/4 |
| 15 | 2/4 | 3/4 | — | 3/4 |
| 16 | 3/4 | 3/4 | — | 3/4 |
| 17 | 3/4 | 3/4 | — | 3/4 |
| 18 | 3/4 | 3/4 | — | 3/4 |

TABLE 1-continued

Data from screening studies at a dose of 100 mg/kg for selected compounds according to the general formula (II).

| Compound | Test* | | | |
|---|---|---|---|---|
| | MES | 6 Hz (32 mA) | 6 Hz (44 mA) | ScPTZ |
| 19 | 3/4 | 4/4 | 2/4 | 3/4 |
| 20 | 4/4 | 3/4 | — | 2/4 |

*Tests carried out in mice after intraperitoneal administration at a time point of 0.5 h, data indicate the number of mice protected in a given seizure model/number of mice tested;
MES-the maximal electroshock test, the 6 Hz (32 mA) and 6 Hz (44 mA) test-the psychomotor seizures induced by low-frequency current (6 Hz) and intensity of 32 mA or 44 mA, respectively;
scPTZ-the subcutaneous seizure test;
"—"-substance not tested.

The above tests were carried out for racemic mixtures of compounds according to the invention.

Table 2 presents quantitative pharmacological data for selected compounds according to general formula (II), in particular for the selected active compound—1-(2-oxo-1-phenyl-2-(4-(3-(trifluoromethyl)phenyl)piperazin-1-yl)ethyl)pyrrolidine-2,5-dione (6), which protected 100% of the mice in the MES test, 6 Hz (32 mA and 44 mA) test and scPTZ test during the screening studies (time point of 0.5 h).

TABLE 2

The $ED_{50}$ and $TD_{50}$ values for selected compounds according to the general formula (II) and the model AED - valproic acid (VPA) after intraperitoneal administration in mice.

| Compound | $ED_{50}$ [mg/kg] | | | | $TD_{50}$ (mg/kg) | PI ($TD_{50}/ED_{50}$) |
|---|---|---|---|---|---|---|
| | MES | 6 Hz (32 mA) | 6 Hz (44 mA) | scPTZ | | |
| 2 | 91.1 | 83.5 | — | 100.0 | >300 | >3.3 (MES) <br> >3.6 (6 Hz, 32 mA) <br> >3.0 (scPTZ) |
| 3 | 36.9 | 39.5 | — | 52.6 | 143.8 | 3.9 (MES) <br> 3.6 (6 Hz) <br> 2.7 (scPTZ) |
| 4 | 68.5 | 17.7 | — | >100 | >300 | >4.4 (MES) <br> >17.0 (6 Hz, 32 mA) |
| 5 | 37.2 | 35.5 | — | 57.6 | 171.0 | 4.6 (MES) <br> 4.8 (6 Hz, 32 mA) <br> 3.0 (scPTZ) |
| 6 | 23.7 | 22.4 | 73.2 | 59.4 | 195.7 | 8.2 (MES) <br> 8.7 (6 Hz, 32 mA) <br> 2.7 (6 Hz, 44 mA) <br> 3.3 (scPTZ) |
| 9 | 97.7 | 63.0 | 195.7 | 94.3 | 274.2 | 2.8 (MES) <br> 4.4 (6 Hz, 32 mA) <br> 1.4 (6 Hz, 44 mA) <br> 2.9 (scPTZ) |
| 10 | 41.7 | 38.3 | — | <60 | 74.0 | 1.8 (MES) <br> 1.9 (6 Hz, 32 mA) <br> >1.2 (scPTZ) |
| 12 | 36.2 | 15.8 | 57.9 | >100 | 150.0 | 4.1 (MES) <br> 9.5 (6 Hz, 32 mA) <br> 2.6 (6 Hz, 44 mA) <br> <1.5 (scPTZ) |
| 13 | 43.9 | 26.2 | — | <100 | 73.6 | 1.7 (MES) <br> 2.8 (6 Hz, 32 mA) <br> >0.7 (scPTZ) |
| 14 | 56.4 | 48.3 | — | <100 | >300 | 5.3 (MES) <br> 6.2 (6 Hz, 32 mA) |
| 19 | 81.8 | 41.0 | — | <100 | 254.3 | 3.1 (MES) <br> 6.2 (6 Hz, 32 mA) <br> >2.5 (scPTZ) |
| VPA | 252.7 | 130.6 | 183.1 | 239.4 | 430.7 | 1.7 (MES) <br> 3.3 (6 Hz, 32 mA) <br> 2.3 (6 Hz, 44 mA) <br> 1.8 (scPTZ) |

The substances were tested 0.5 h after intraperitoneal administration;
MES—the maximal electroshock test, the 6 Hz (32 mA) and 6 Hz (44 mA) test - the psychomotor seizures induced by low-frequency current (6 Hz) and intensity of 32 mA or 44 mA, respectively;
scPTZ—the subcutaneous seizure test;
$TD_{50}$ values were obtained in the rotarod test;
PI—protective index ($TD_{50}/ED_{50}$);
"—"—substance not tested.

The obtained results confirmed that the compounds of the invention, especially compound 6, have a potent protective effect and distinctly more favorable protective indexes in comparison to the model AED—valproic acid. Notably, valproic acid is known to possess wide spectrum of therapeutic indications.

Example 33. Determination of Antinociceptive Activity in the In Vivo Studies in Mice The tests were carried out using male white Swiss mice (CD-1) weighing 18-25 g. All procedures were carried out in accordance with Polish and international guidelines on ethics of animal testing, after obtaining appropriate institutional approval. The study group consisted of 8-10 animals. The tested and reference substances were administered intraperitoneally 30 minutes before given test as suspension in 1% aqueous solution of Tween. All tests/models were carried out based on the procedures described in the specialist literature: the formalin test (Beirith, A.; Santos, A. R.; Calixto, J. B.; Rodrigues, A. L.; Creczynski-Pasa, T. B. *Eur. J. Pharmacol.* 1998, 345, 233-245), the model of capsaicin-induced pain (Mogilski, S.; Kubacka, M.; Redzicka, A.; Kazek, G.; Dudek, M.; Malinka, W.; Filipek, B. *Pharmacol. Biochem. Behav.* 2015, 133, 99-110), the model of oxaliplatin-induced neuropathic pain—von Frey test (Sałat, K.; Cios, A.; Wyska, E.; Satat, R.; Mogilski, S.; Filipek, B.; Wigękowski, K.; Malawska, B. *Pharmacol. Biochem. Behav.* 2014, 122, 173-181).

Example 34. Determination of Analgesic Activity in the Formalin Test

The pain was induced by the subplantar injection of 20 µL of 2.5% formalin solution into the mice right hind paw. The animals were placed in separate, transparent observation chambers for a period of 30 minutes. The measured value was the total licking and biting time of the paw to which the formalin solution was injected. The nociceptive reaction time was calculated for the first 5 minutes after formalin injection (first phase of the test—acute pain) and in the 15-20, 20-25 and 25-30 minutes time intervals after its administration (second phase of the test—inflammatory pain). The observed inhibition of nociceptive reaction—reduction of paw licking and biting time, was interpreted as the analgesic effect of the compound tested. Based on the results obtained, the $ED_{50}$ dose was calculated (dose that reduces the nociceptive reaction time by 50%). The reference compound in this test was valproic acid, which was administered intraperitoneally at doses of 100 mg/kg, 150 mg/kg and 200 mg/kg. Compound 6 was administered at doses of 10 mg/kg, 20 mg/kg and 30 mg/kg.

Compound 6 showed distinct analgesic activity in both phases of the test. The mean nociceptive response time in the control group was 90.0±4.97 seconds and 212.70±10.16 seconds in the first and second phase of the test, respectively. Compound 6, at all doses tested, reduced the nociceptive reaction time in the first phase of the formalin test, corresponding to acute pain, with a statistically significant effect observed at the two highest doses. The $ED_{50}$ value for compound 6 in the first phase of the test was 28.50 mg/kg. In the second phase of the test corresponding to tonic inflammatory pain, compound 6, at all doses used, statistically significantly shortened the time of nociceptive reaction. The $ED_{50}$ value in the second phase of the test for this compound was 12.40 mg/kg (FIG. 3).

Valproic acid (VPA) showed no analgesic activity in the first phase of the test at any of the doses tested. In the second phase of the VPA test, the nociceptive response time was reduced at all doses used, and the $ED_{50}$ value in this phase of the test was 132.90 mg/kg (FIG. 3).

Example 35. Determination of Analgesic Activity in the Capsaicin Pain Model

This test assesses the time of licking and/or biting the hind paw into which mice were injected subplantarly with capsaicin in an amount of 1.6 µg, dissolved in 20 µl of a mixture containing 0.9% saline and ethanol (5% of the final volume). Observation was carried out for minutes after capsaicin administration. Test compounds were administered intraperitoneally 30 minutes before administration of capsaicin. Inhibition of nociceptive reaction—shortening the time of licking and biting the paw was the measure of antinociceptive activity of the compound tested.

Valproic acid (VPA) was the reference compound in this test. VPA was administered intraperitoneally at doses of 100 mg/kg, 150 mg/kg and 200 mg/kg. Compound 6 was administered at 20 mg/kg, 30 mg/kg and 40 mg/kg. Test compounds were administered as a suspension in 1.0% Tween 80 solution. The control group consisted of mice treated with vehicle alone (1% Tween 80 solution). The nociceptive reaction time in this group was 43.29±3.21 seconds.

Compound 6 in statistically significant manner reduced the nociceptive response time at 20 mg/kg and 30 mg/kg, and the $ED_{50}$ was 17.9 mg/kg (FIG. 4)

The reference compound (valproic acid) statistically significantly reduced the nociceptive reaction time to 25.00±4.57 seconds (corresponding to an analgesic activity of 42.25%), only after the 200 mg/kg dose (FIG. 4).

Example 36. Determination of Analgesic Activity in the Model of Oxaliplatin-Induced Neuropathic Pain—Von Frey Test Oxaliplatin (OXPT) was dissolved in a 5% glucose solution, followed by intraperitoneal administration to mice. A single dose of 10 mg/kg was used. Tactile and thermal (sensation of low temperature) allodynia associated with oxaliplatin-induced neuropathy are characterized by two phases. The early phase is acute and develops soon after administration of the OXPT, while the symptoms of the later (chronic) phase (associated with neurons damage), develops after a few days. Behavioral tests in mice with OXPT-induced neuropathy were carried out 7 days after its administration, i.e. in the late phase of neuropathy.

The influence of compounds tested on tactile allodynia was determined in the von Frey test. The animals were placed individually in cages with a reticulated bottom, 60 minutes before the beginning of the experiment, in order to adapt to the new environment. An electronic Von Frey apparatus (Electronic Von Frey, Bioseb, France) was used to assess the pain threshold for mechanical stimuli. The von Frey's fiber was applied to the underside of the right mouse paw with increasing pressure. The crossing of pain threshold resulted in the paw withdrawal and subsequent recording of the mechanical pressure that evoked the nocifensive response. The measurement was performed 3 times for each mouse, with at least 30 seconds between the measurements, then the results obtained were averaged. The entire study was performed 3 times: before OXPT administration to determine the baseline pain threshold; 7 days after administration of OXPT, and before administration of test compounds, to assess developing neuropathy by setting a new pain threshold; 30 minutes after administration of the compounds to determine their influence developed neuropathy.

The effect of the test compound on thermal allodynia was evaluated in a Cold Plate test using specialized equipment— Cold/Hot Plate; Bioseb, France. The animals were placed individually on a metal plate cooled to 2° C. using the thermostated device. The observed nociceptive reactions of animals included licking and/or characteristic hind paw lift or bounce. The observation time was set at 60 s to eliminate the potential risk of tissue damage and minimize animal discomfort. Similar to the Von Frey test, the measurement was performed 3 times.

Compound 6 and valproic acid as a reference AED were administered intraperitoneally as a suspension in a 1% solution of Tween 80. Compound 6 was administered at doses of 10, 20 and 30 mg/kg. The reference compound (valproic acid) was given at doses of 50, 100 and 150 mg/kg.

Injection of OXPT in mice caused development of neuropathy resulting in a prominent and statistically significant reduction in the pain threshold as measured by the von Frey method. The pain sensitivity threshold decreased from 3.18±0.06-3.36±0.10 g in healthy mice to a level in the range 1.89±0.04-1.94±0.14 g in OXPT-administered mice. The obtained results indicate a statistically significant analgesic effect of the tested compound 6. The average pain sensitivity threshold in the control group was 3.36±0.10 g, whereas after the administration of OXPT it decreased to 1.89±0.04 g (56.25% of the initial value). Administration of compound 6 at a dose of 10 mg/kg increased the pain threshold to 2.87±0.12 g (85.41% of the initial value), which indicates the inhibitory effect on the development of mechanical allodynia already at low doses. The dose of 20 mg/kg of compound 6 caused an increase in pain sensitivity threshold to 3.83±0.13 g, which is 113.98% of the initial value. The 30 mg/kg dose resulted in an increase in pain threshold to 4.17±0.17 g, which is 124.10% of the initial value. The results obtained indicate that compound 6 is highly effective in suppressing of mechanical allodynia development which is the result of neurons damage caused by the chemotherapeutic agent—OXPT (FIG. 5A).

The average pain sensitivity threshold in the control group for the reference compound (valproic acid, VPA) was 2.62±0.06 g, and after the administration of OXPT it decreased to 1.78±0.04 g. Administration of VPA at a dose of 150 mg/kg caused an increase in the pain threshold up to 3.97±0.30 g, while doses of 100 mg/kg and 50 mg/kg body weight allowed to achieve an increase in the average pain threshold to 3.18±0.14 g and 2.75±0.06 g, respectively (FIG. 5B).

Compound 6 also significantly increased thermal allodynia sensitivity in the cold plate test (FIG. 5C).

Example 37. In Vitro Affinity and Functional Studies

The affinity and functional tests performed in vitro for the most active substance 6, representing compounds according to formula (II), showed that their mechanism of action is associated with the effect on neuronal conductivity through interaction with voltage-dependent sodium channels (site 2) and calcium channels (dihydropyridine, diltiazem and verapamil binding sites). A unique feature of the compound 6 representing compounds of formula (II) according to the invention is the inhibition of calcium currents by blocking the transient receptor potential vanilloid type 1 (TRPV1). This effect has not been disclosed for known AEDs. TRPV1 receptor antagonism may determine the antinociceptive effect of the compounds disclosed herein. The role of the TRPV1 receptor in conduction of pain stimuli has been well documented in specialist literature (Szallasi, A.; Cortright, D. N.; Blum, C. A.; Eid, S. R. Nat. Rev. Drug. Discov. 2007, 6, 357-372). The compounds according to the invention are characterized by a complex mechanism of action, which is not described for known anticonvulsants. It should be emphasized, however, that further in vitro studies may reveal further molecular targets responsible for the pharmacological action of substances being the subject of current patent claim. The results of binding studies (sodium channel, calcium channel) and functional tests (TRPV1 receptor) for compound 6 are shown in Table 3.

TABLE 3

In vitro affinity/functional tests results for compound 6, representing substances according to formula (II) of the invention*

| Affinity studies | Material | Inhibition of specific control binding (concentration tested [μM])$_g$ |
|---|---|---|
| Na$_+$ channel (miejsce 2)$_a$ | Rat cerebral cortex | 82.5 (100) 33.4 (10) |
| Ca$_{2+}$ channel type L (dihydropyridine binding site)$_b$ | Rat cerebral cortex | 82.3 (100) 30.8 (10) |
| Ca$_{2+}$ channel type L (diltiazem binding site)$_c$ | Rat cerebral cortex | 69.6 (100) |
| Ca$_{2+}$ channel type L (verapamil binding site)$_d$ | Rat cerebral cortex | 58.2 (100) |
| Potassium channel (hERG)$_e$ | Human recombinant cells (HEK-293) | 25.8 (100) |
| Functional studies | | % Inhibition of agonist control responses (concentration tested [μM])$_a$ |
| TRPV1 receptor (VR1) (h) (antagonist effect)$_f$ | Human recombinant cells (CHO) | 71.7 (100) |

*The tests were carried out in CEREP laboratories (France) according to the procedures described in the literature:
$_a$Brown, G. B. J. Neurosci. 1986, 6, 2064-2070;
$_b$Gould, R. J.; Murphy, K. M.; Snyder, S. H. Proc. Natl. Acad. Sci. USA. 1982, 79, 3656-3660;
$_c$Schoemaker, H.; Langer, SZ. Eur. J. Pharmacol. 1985, 111, 273-277;
$_d$Reynolds, I. J.; Snowman, A. M.; Snyder, S. H. J. Pharmacol. Exp. Ther. 1986, 237, 731-738;
$_e$Huang, X. P.; Mangano, T.; Hufeisen, S.; Setola, V.; Roth, B. L. Assay Drug Dev. Technol. 2010, 8, 727-742;
$_f$Phelps, P. T.; Anthes, J. C.; Correll, C. C. Eur. J. Pharmacol. 2005, 513, 57-66;
g% inhibition >50% is considered as significant effect exerted by the compound.

Example 38. In Vitro Electrophysiological Studies

The experiments were carried out in accordance with institutional and international guidelines regarding the ethics of animal research. Rats (3 weeks old) were anesthetized with ethyl chloride and decapitated. The brains were then removed and placed in ice-cold extracellular fluid. The methodology of slice preparation and pre-incubation has been described earlier (Szulczyk, B.; Nurowska, E. Biochem. Biophys. Res. Commun. 2017, 491, 291-295). The sections containing the prefrontal cortex were enzymatically and mechanically dispersed. Single prefrontal cortex pyramidal neurons were visualized using an inverted microscope (Nikon). Sodium currents were induced by rectangular depolarizing stimuli. The potential between depolarizing stimuli was maintained at −65 mV.

The intracellular fluid in the pipette contained (in mM): CsF (110), NaCl (7), EGTA (3), HEPES-Cl (10), MgCl$_2$ (2), Na$_2$ATP (4) (pH 7.4 and osmolarity 290 mOsm).

The extracellular fluid washing the neurons contained (in mM): NaCl (30), choline chloride (90), TEA-Cl (30), CaCl$_2$ (2), MgCl$_2$ (2), glucose (15), HEPES (10), LaCl$_3$ (0.001) and CdCl$_2$ (0.4) (pH 7.4). Currents were recorded using an Axopatch 1D amplifier and analyzed using pClamp software (Axon Instruments and Molecular Devices, USA). Pipette resistance was between 4 and 5 MΩ. After gigaseal formation, pipette capacitance was compensated by means of an amplifier.

The patch membrane was ruptured by suction or by an electrical stimulus, and then membrane capacitance was compensated. Access resistance was between 5 and 7 MΩ. A series resistance compensation of 80% was used. The leakage current was subtracted from the recorded currents. Recordings were carried out at room temperature. Voltage-dependent potassium currents were blocked by TEA-Cl in the extracellular fluid. Voltage-dependent calcium currents were blocked by cadmium and lanthanum ions in the extracellular fluid. The neuron's membrane potential was maintained at −65 mV. Substance 6 was administered from the extracellular side (to the whole bath).

The obtained results confirmed the inhibitory effect of compound 6 on rapidly activating and rapidly inactivating voltage-dependent sodium channels in the prefrontal cortex pyramidal neurons (tests were performed at a concentration of 100 µM). Maximum currents were induced by rectangular depolarizing stimuli lasting 20 msec. The potential between depolarizing stimuli was maintained at −65 mV. Control recordings were carried out for 2 minutes, the test substance was administered for 3 minutes and the currents after washing out were recorded for 5 minutes. Recorded currents were normalized to the value of control currents. Substance 6 blocked the maximum amplitude of sodium currents up to 0.59±0.08 compared to the control (1.0, p<0.001). After washing out, the current amplitude partially returned to control values (0.79±0.07, n=5). Examples of sodium current recordings and averaged results are shown in FIG. 6.

Example 39. Evaluation of ADMETox Parameters in In Vitro Studies

The ADME-Tox parameters of compound 6 were estimated by in vitro methods using recombinant enzymes, human and mouse liver microsomes, and eukaryotic cell lines.

Metabolic stability. The metabolic stability of compound 6 was evaluated using human liver microsomes (HLMs). Internal clearance values $CL_{int}$ were calculated by monitoring changes in compound concentration in the presence of microsomes per unit of time, according to the procedure proposed by Obach R. S. (Obach, R. S. *Drug Metab. Dispos.* 1999, 27, 1350-1359). Based on the data obtained, an extremely low clearance value of compound 6 after incubation with HLMs was found, amounting to $CL_{int}$=5.8 ml/min/kg, indicating its predicted high stability in the human body. UPLC analysis of the metabolism of compound 6 after incubation with HMLs revealed that it is metabolized to three metabolites M1-M3 (FIG. 7). Based on the UPLC/MS data, it was found that the metabolite M1 is formed by dehydrogenation of the piperazine ring, M2 is formed by hydroxylation of the phenyl substituent linked to piperazine, while M3 is probably formed as a result of hydroxylation of the side phenyl group with simultaneous reduction of the ketone to hydroxyl group in the imide fragment (FIG. 7).

Metabolic stability tests—methodology. Metabolic stability studies for compound 6 were performed using HLMs (Promega, Madison, WI, USA). For this purpose, 10 µL of compound 6 at a concentration of 1000 µM was diluted with 132 µL with tris-HCl buffer (100 mM, pH 7.4), followed by the addition of 8 µL of appropriate microsomes. The reaction mixture was preincubated at 37° C. for 5 minutes, followed by the addition of 50 µL of NADPH Regeneration System, supplied by Promega (Madison, WI, USA). After mixing, the whole mixture was incubated at 37° C. for 120 minutes. To complete the reaction, 200 µL of cold methanol was added to the tubes and centrifuged. The supernatant was subjected to UPLC/MS analysis, including fragmentation analysis. Four mixtures of 6 with HLMs were prepared to determine the internal clearance $CL_{int}$. Each of these reactions was completed at a different time point, after 5, 15, 30 and 45 min, by the addition of cold methanol containing 50 µM internal standard. Then, according to literature guidelines (Obach, R. S. *Drug Metab. Dispos.* 1999, 27, 1350-1359), based on the plot of the relationship between the height of the peak from 6 and the height of the internal standard, the regression equation was determined and the reaction rate constant k was calculated. Then the constant k was substituted to equation (1).

$$t_{1/2} = \frac{\ln 2}{-k} \quad (1)$$

The calculated $t_{1/2}$ value was then substituted into equation (2):

$$CL_{int(human)} = \frac{0.693}{\text{in vitro } t_{1/2}} \times \frac{\text{mL of mixture}}{\text{mg of microsomes}} \times \frac{45 \text{ mg of microsomes}}{\text{g of liver}} \times \frac{20 \text{ g of liver}}{\text{kg of body weight}} \quad (2)$$

Impact on Pgp activity. P-glycoprotein (Pgp) is an integral plasma membrane protein that, as an ATP-dependent burst pump, actively removes xenobiotics and can cause drug interactions. Pgp plays an important role in the absorption of drugs in the gastrointestinal tract and also through the blood-brain barrier. A commercial bioluminescent Pgp-Glo™ Assay System test (Promega, Madison, WI, USA) was used to study the effect of compound 6 on Pgp activity. The operation of the test is based on measuring changes in the level of ATP consumed by membranes containing the recombinant Pgp protein in the presence of test compounds. The results were presented as % of baseline activity and compared to reference compounds: selective Pgp inhibitor $Na_3VO_4$ and verapamil stimulator. Compound 6 showed a statistically significant (p<0.01) inhibitory effect on Pgp up to 38% of baseline activity at 100 µM, while no effect on Pgp activity at 50 µM was noted (FIG. 8)

Impact on Pgp activity—methodology. The tests were performed according to the protocol of the bioluminescent Pgp-Glo™ Assay System test provided by the Promega company (Madison, WI, USA). Enzyme reactions were performed in Nunc™ MicroWell™ 96-well white plates from Thermo Scientific (Waltham, MA, USA). Bioluminescence was measured with a PerkinElmer multispecific EnSpire plate reader (Waltham, MA USA). After using the $Na_3VO_4$ Pgp inhibitor (induces 100% inhibition), there was an increase in signal relative to the control sample, indicating inhibition of ATP consumption by Pgp, the so-called base activity. The calculated difference between the luminescence values of the inhibitor-treated sample and the control sample was taken as 100% of the Pgp base activity and treated as a negative control in the test. The reference compounds $Na_3VO_4$ and verapamil were used at 100 μM and 200 μM, respectively, according to the manufacturer's instructions. Compound 6 was tested at 50 and 100 μM concentrations obtained after dilution of concentrated stock solution (10 mM) in DMSO in reaction buffer. Incubation of the compounds with Pgp-containing membranes was carried out for 40 minutes at 37° C., followed by bioluminescence measurement to determine the degree of ATP consumption by Pgp. Statistical significance was calculated by one-way ANOVA variance analysis and the Bonferroni method using GraphPad Prism 5. The compounds were tested in triplicate.

Effect of compound 6 on cytochrome P-450 3A4 and 2D6 activity. The research was conducted using commercial luminescence tests CYP3A4 P450-Glo™ and CYP2D6 P450-Glo™ from Promega (Madison, WI, USA) based on the methodology described in the literature (Socała, K.; Mogilski, S.; Pieróg, M.; Nieoczym, D.; Abram, M.; Szulczyk, B.; Lubelska, A.; Latacz, G.; Doboszewska, U.; Wlaź, P.; Kamiński, K. ACS Chem. Neurosci. 2018, doi: 10.1021/acschemneuro.8b00476; Latacz, G.; Lubelska, A.; Jastrzębska-Więek, M.; Partyka, A.; Sobato, A.; Olejarz, A.; Kucwaj-Brysz, K.; Satata, G.; Bojarski, A. J.; Wesołowska, A.; Kieć-Kononowicz, K.; Handzlik, J. Chem. Biol. Drug. Des. 2017, 90, 1295-1306). The CYP isoforms selected for study are responsible for the metabolism of approximately 40-50% of the drugs available on the market, and their stimulation or inhibition determines the majority of metabolic drug interactions. The results obtained indicate no effect of compound 6 on CYP3A4 activity (FIG. 9A) and a very weak stimulating effect on CYP2D6 (FIG. 9B) at a concentration of 10 μM. In summary, the results obtained indicate a low probability of potential metabolic interactions caused by 6.

In vitro hepatotoxicity assessment. The studies were conducted using the hepatoma HepG2 liver cancer cell line, which is used to assess the hepatotoxicity of the substance in vitro. A classic MTS colorimetric assay from Promega (Madison, WI, USA) was used to investigate the effect of 6 on HepG2 cell viability and proliferation. The compound was tested at four concentrations in the range (0.1-100 μM). Doxorubicin at a concentration of 1 μM was used as a reference cytostatic. In addition, the reference mitochondrial toxin carbonyl cyanide m-chlorophenylhydrazone (CCCP) at a concentration of 10 μM was also used (FIG. 10). Hepatotoxicity studies after 72 h incubation of the HepG2 line with compound 6 showed a statistically significant ($p<0.05$) reduction in cell viability only for the highest concentration of 100 μM used in the study (FIG. 10). In addition, cell viability was reduced to just 84% of the control, indicating a trace toxic effect of this compound on HepG2 cell lines. Due to the particular exposure of liver cells to the potential toxic effects of xenobiotics, an additional test was carried out with the HepG2 line in the form of luminescent measurement of ATP levels in cells, after a short 3-hour exposure to compound 6, in concentrations in the range of 1-100 μM. For this purpose, a commercial CellTiter-Glo Luminescent Cell Viability Assay from Promega (Madison, WI, USA) was used. The aim of the study was to check the effect of the compound on mitochondrial respiration of hepatoma cells. The reference point was the CCCP reference mitochondrial toxin at a concentration of 10 μM. There was no statistically significant effect of Compound 6 on ATP levels in HepG2 cells, even at the highest concentration of 100 μM used. This indicates a very low risk of hepatotoxic effect of compound 6 (FIG. 11).

In vitro hepatotoxicity assessment—methodology. HepG2 hepatoma cell line (ATCC HB-8065) was used for the studies. The HepG2 line was incubated in "Modified Eagle's Medium" (MEM) culture medium with the addition of 2 mM glutamine and 10% FBS from Gibco (Carlsbad, CA, USA). Cells were incubated at 37° C. in an atmosphere containing 5% $CO_2$. CellTiter 96® AQueous Non-Radioactive Cell Proliferation Assay (MTS) supplied by Promega (Madison, WI, USA) was used to test cell viability. Prior to testing, cells were placed on Thermo Scientific Nunc™ 96-well transparent culture plates (Waltham, MA, USA) at a concentration of $1.5 \times 10^4$ cells per well and incubated for 24 h. Then a 10 mM stock solution of compound 6 was diluted. in the appropriate culture medium and added to the cells at final concentrations in the range of 0.1-100 μM (DMSO concentration in all wells was 1%). Reference compounds CCCP and DX were applied at final concentrations of 10 μM and 1 μM, respectively. After 72 h incubation at 37° C. in an atmosphere containing 5% $CO_2$, the medium with the compound was removed, followed by the addition of fresh medium with diluted MTS reagent. Plates were again incubated for 2-3 hours, followed by absorbance measurement at 490 nm with an EnSpire PerkinElmer (Waltham, MA, USA) reader. Statistical significance was calculated by one-way ANOVA variance analysis and the Bonferroni method. The compounds were tested in four replications.

CellTiter-Glo Luminescent Cell Viability Assay from Promega (Madison, WI, USA) was used to study ATP levels in HepG2 cells. Prior to testing, the cells were plated into white, 96-well transparent bottom culture plates from Corning (Tewksbury, MA, USA), adapted for luminescence measurement at a concentration of $1.5 \times 10^4$ cells per well. Then, the cells were incubated at 37° C. in an atmosphere containing 5% $CO_2$. Compound 6 was applied to the plate at three final concentrations of 1, 10 and 100 μM, CCCP at 10 μM and DX at 1 μM, and the amount of 100 μL. The plate was incubated for 3 h at 37° C. and 5% $CO_2$. Luminescence measurement was carried out with an EnSpire PerkinElmer (Waltham, MA, USA) reader after adding CellTiter-Glo Luminescent Cell Viability Assay in an amount of 100 μl to the culture. Statistical significance was calculated by one-way ANOVA and Bonferroni analysis using GraphPad Prism 5. All substances were tested in four replications.

Example 40. Preparation of Selected Enantiomers of Compounds According to the Invention Enantiomers of compounds according to formula (II) of the invention can be obtained applying four-stage procedure using commercially available tert-butoxycarbonyl (Boc) D- or L-amino acid derivatives (R or S absolute configuration, respectively) as starting materials. Enantiomers were obtained for selected compounds described by formula (II) for which k=0, A and B have the meaning as in the case of racemic mixtures of formula (II).

A general scheme for the synthesis of enantiomers of compounds according to formula (II) is shown in FIG. 12.

In the first stage, the condensation reaction of given piperazine derivative with the corresponding Boc-D- or Boc-L-amino acid derivative yields an intermediate product of formula (VII), which subsequently forms the amine derivative (VI) in the deprotection reaction. In the next step, compound (VI) is condensed with succinic anhydride to obtain the intermediate with the amide-acid structure (V), which next undergoes cyclization reaction to form compound R-(II) or S-(II). Asymmetric synthesis proceeds with retention of absolute configuration that was confirmed applying crystallographic analysis.

Examples of synthesis as well as physicochemical and spectral data for selected intermediates (VII, VI, and V according to FIG. 12) are described below.

Example 41. Tert-butyl-(R)-(2-oxo-1-phenyl-2-(4-(3-(trifluoromethyl)phenyl)piperazin-1-yl)ethyl)carbamate (VII)

Boc-D-phenylglycine (1.25 g, 5 mmol, 1 eq) was dissolved in 20 mL of DCM, followed by the addition of DCC (1.55 g, 7.5 mmol 1.5 eq). Next after 30 minutes 1-(3-(trifluoromethyl)phenyl)piperazine (1.15 g, 5 mmol, 1 eq) dissolved in 5 mL of DCM was added. The reaction was continued with stirring at room temperature for 4 hours. After this time, DCM was distilled off to dryness. Intermediate VII was purified by column chromatography using DCM:MeOH (9:0.5; v/v) eluent system.

Light oil. Yield: 78% (1.81 g); TLC: $R_f$=0.62 (DCM:MeOH (9:0.5; v/v)); $C_{24}H_{28}F_3N_3O_3$ (463.50), Monoisotopic mass: 463.21. UPLC (100% purity): $t_R$=8.40 min. $(M+H)^+$ 464.2.

Example 42. (R)-2-Amino-2-phenyl-1-(4-(3-(trifluoromethyl)phenyl)piperazin-1-yl)ethan-1-one (VI)

5 mL of TFA was added to the tert-butyl-(R)-(2-oxo-1-phenyl-2-(4-(3-(trifluoromethyl)phenyl)piperazin-1-yl)ethyl)carbamate solution (VII, 1.39 g, 3 mmol, 1 eq) in DCM (50 mL) and stirred for 2 hours. The reaction mixture was then neutralized with a 25% $NH_4OH$ solution, followed by extraction with DCM (3×50 mL). The organic layer was dried over anhydrous $Na_2SO_4$ and then evaporated to dryness. (R)-2-Amino-2-phenyl-1-(4-(3-(trifluoromethyl)phenyl)piperazin-1-yl)ethan-1-one was obtained as a yellow oil.

Yellow oil. Yield: 95% (1.03 g); $C_{19}H_{20}F_3N_3O$ (363.38), Monoisotopic mass: 363.16. UPLC (purity>99.9%): $t_R$=4.96 min. $(M+H)^+$ 364.1.

Example 43. (R)-4-Oxo-4-((2-oxo-1-phenyl-2-(4-(3-(trifluoromethyl)phenyl)piperazin-1-yl) ethyl)amino)butanoic acid (V)

Succinic anhydride (0.28 g 2.8 mmol, 1 eq) was added to a solution of (R)-2-amino-2-phenyl-1-(4-(3-(trifluoromethyl)phenyl)piperazin-1-yl)ethan-1-one (VI, 1.02 g 2.8 mmol, 1 eq) in AcOEt (50 mL) and the mixture was stirred for 30 minutes. After this time, the solvent was distilled off to dryness. The compound was obtained in solid form after washing with $Et_2O$.

White solid. Yield: 87% (1.13 g); $C_{23}H_{24}F_3N_3O_4$ (463.46), Monoisotopic mass: 463.17. UPLC (purity>99.9%): $t_R$=6.40 min. $(M+H)^+$ 464.2.

Example 44. (R)-1-(2-(4-(3-chlorophenyl)piperazin-1-yl)-2-oxo-1-phenylethyl)pyrrolidine-2,5-dione ((R)-3)

$ZnCl_2$ (0.27 g, 2.0 mmol, 1 eq) was added to the suspension of (R)-4-((2-(4-(3-chlorophenyl)piperazin-1-yl)-2-oxo-1-phenylethyl)amino)-4-oxobutanoic acid (V, 0.86 g, 2.0 mmol, 1 eq) in dry benzene (50 mL) and the whole mixture was heated to 80° C., then HMDS solution (0.48 g, 0.62 ml, 3.0 mmol, 1.5 eq) in dry benzene (5 ml) was added dropwise over 30 minutes. The reaction was continued with stirring in reflux for about 24 hours and then concentrated under reduced pressure. After distilling off the solvent, the oily residue was dissolved in DCM and extracted with 0.1 M HCl (3×50 mL), water (3×50 mL) and saturated NaCl solution (3×50 mL). The organic layer was dried over anhydrous $Na_2SO_4$ and then evaporated to dryness. The crude product was purified by column chromatography using DCM:MeOH (9:0.3; v/v) eluent system. The compound was obtained as a solid after washing with $Et_2O$.

White solid. Yield: 82% (0.67 g); m.p. 167.3-168.1° C.; TLC: $R_f$=0.41 (DCM:MeOH (9:0.3; v/v)); $C_{22}H_{22}ClN_3O_3$ (411.89), Monoisotopic mass: 411.13. UPLC (purity: >99.9%): $t_R$=6.70 min, $(M+H)^+$412.4. $^1$H NMR (500 MHz, $CDCl_3$) δ 2.64-2.75 (m, 5H), 2.96-3.12 (m, 2H), 3.21-3.37 (m, 3H), 3.60-3.72 (m, 1H), 3.92-4.03 (m, 1H), 6.10 (s, 1H), 6.68 (dd, J=8.0, 2.3 Hz, 1H), 6.77 (t, J=2.0 Hz, 1H), 6.81 (d, J=7.6 Hz, 1H), 7.13 (t, J=7.9 Hz, 1H), 7.32-7.37 (m, 3H), 7.42 (d, J=6.8 Hz, 2H). $^{13}$C NMR (126 MHz, $CDCl_3$) δ 28.1, 42.3, 45.6, 48.5, 48.8, 56.9, 114.5, 116.4, 120.3, 128.8, 129.0, 129.9, 130.2, 133.0, 135.1, 151.8, 165.1, 176.4. Enantiomeric purity>99% ($t_R$=40.25 min).

Example 45. (R)-1-(2-(4-(3,5-dichlorophenyl)piperazin-1-yl)-2-oxo-1-phenylethyl)pyrrolidine-2,5-dione ((R)-4)

The compound was prepared according to procedure described in Example 44. (R)-4-((2-(4-(3,5-dichlorophenyl)piperazin-1-yl)-2-oxo-1-phenylethyl)amino)-4-oxobutanoic acid (0.93 g, 2 mmol, 1 eq) was used as the starting material for the cyclization reaction. The crude product was purified by column chromatography using DCM:MeOH (9:0.2; v/v) eluent system.

White solid. Yield: 79% (0.70 g); m.p. 174.3-175.5° C.; TLC: $R_f$=0.43 (DCM:MeOH (9:0.2; v/v)); $C_{22}H_{21}Cl_2N_3O_3$ (446.33), Monoisotopic mass: 445.10. UPLC (purity: >99.9%): $t_R$=7.59 min, $(M+H)^+$ 446.1. $^1$H NMR (500 MHz, $CDCl_3$) δ 2.64-2.74 (m, 5H), 2.99-3.03 (m, 1H), 3.06-3.11 (m, 1H), 3.23-3.31 (m, 2H), 3.43-3.47 (m, 1H), 3.60-3.64 (m, 1H), 3.95-3.99 (m, 1H), 6.08 (s, 1H), 6.63 (d, J=1.7 Hz, 2H), 6.79 (t, J=1.4 Hz, 1H), 7.32-7.37 (m, 3H), 7.41 (d, J=6.7 Hz, 2H). $^{13}$C NMR (126 MHz, $CDCl_3$) δ 28.1, 42.1, 45.4, 47.9, 48.2, 56.8, 114.3, 119.8, 128.8, 129.1, 129.9, 132.9, 135.6, 152.1, 165.2, 176.4. Enantiomeric purity>99% ($t_R$=43.23 min).

Example 46. (R)-1-(2-Oxo-1-phenyl-2-(4-(3-(trifluoromethyl)phenyl)piperazin-1-yl)ethyl) pyrrolidine-2,5-dione ((R)-6)

The compound was prepared according to procedure described in Example 44. (R)-4-Oxo-4-((2-oxo-1-phenyl-2-(4-(3-(trifluoromethyl)phenyl)piperazin-1-yl)ethyl)amino)-butanoic acid (0.93 g, 2.0 mmol, 1 eq) was used as the starting material for the cyclization reaction. The crude product was purified by column chromatography using DCM:MeOH (9:0.5; v/v) eluent system.

White solid. Yield: 80% (0.71 g); m.p. 189.1-190.5° C.; TLC: $R_f$=0.35 (DCM:MeOH (9:0.5; v/v)); $C_{23}H_{22}F_3N_3O_3$ (445.44), Monoisotopic mass: 445.16. UPLC (purity: >99.9%): $t_R$=6.93 min, $(M+H)^+$446.2. $^1$H NMR (300 MHz, $CDCl_3$) δ 2.52-2.85 (m, 5H), 2.99-3.19 (m, 2H), 3.22-3.45 (m, 3H), 3, 62-3.76 (m, 1H), 3.93-4.07 (m, 1H), 6.12 (s, 1H), 6.90-7.15 (m, 3H), 7.11 (d, 1H, J=7.7 Hz), 7.28-7.55 (m, 6H); $^{13}$C NMR (75 MHz, $CDCl_3$) δ 28.0, 42.3, 45.5, 48.4, 48.6, 56.8, 112.7 (d, J=3.4 Hz), 116.7 (d, J=3.4 Hz), 119.2, 124.1 (q, J=272.9 Hz), 128.7, 128.9, 129.7, 129.8, 130.9, 131.5 (q, J=32.2 Hz), 132.8, 150.8, 165.1, 176.4. Enantiomeric purity>99% ($t_R$=39.97 min).

Example 47. (S)-1-(2-Oxo-1-phenyl-2-(4-(3-(trifluoromethyl)phenyl)piperazin-1-yl)ethyl) pyrrolidine-2,5-dione ((S)-6)

The compound was prepared according to procedure described in Example 44. (S)-4-oxo-4-((2-oxo-1-phenyl-2-(4-(3-(trifluoromethyl)phenyl)piperazin-1-yl)ethyl)amino)-butanoic acid (0.93 g, 2.0 mmol, 1 eq) was used as the substrate for the cyclization reaction. The crude product was purified by column chromatography using DCM:MeOH (9:0.5; v/v) eluent system.

White solid. Yield: 78% (0.69 g); m.p. 188.9-190.5° C.; TLC: $R_f$=0.36 (DCM:MeOH (9:0.5; v/v)); $C_{23}H_{22}F_3N_3O_3$ (445.44), Monoisotopic mass: 445.16. UPLC (purity: >99.9%): $t_R$=6.94 min, (M+H)$^+$ 446.2. $^1$H NMR (300 MHz, CDCl$_3$) δ 2.56-2.83 (m, 5H), 3.00-3.20 (m, 2H), 3.23-3.43 (m, 3H), 3.62-3.76 (m, 1H), 3.94-4.08 (m, 1H), 6.12 (s, 1H), 6.89-6.99 (m, 2H), 7.10 (d, 1H, J=7.7 Hz), 7.28-7.53 (m, 6H); $^{13}$C NMR (75 MHz, CDCl$_3$) δ 28.0, 42.2, 45.5, 48.4, 48.6, 56.8, 112.7 (d, J=4.6 Hz), 116.7 (d, J=4.6 Hz), 124.1 (q, J=272.9 Hz), 128.7, 129.0, 129.7, 129.8, 131.6 (q, J=32.2 Hz), 132.8, 150.8, 165.1, 176.3. Enantiomeric purity>99% ($t_R$=26.21 min).

Example 48. (R)-1-(2-Oxo-1-phenyl-2-(4-(3-(trifluoromethoxy)phenyl)piperazin-1-yl)ethyl)pyrrolidine-2,5-dione ((R)-10)

The compound was prepared according to procedure described in Example 44. (R)-4-oxo-4-((2-oxo-1-phenyl-2-(4-(3-(trifluoromethoxy)phenyl)piperazin-1-yl)ethyl)amino)butanoic acid (0.96 g, 2.0 mmol, 1 eq) was used as starting material for the cyclization reaction. The crude product was purified by column chromatography using DCM:MeOH (9:0.5; v/v) eluent system.

White solid. Yield: 77% (0.70 g); m.p. 168.2-169.1° C.; TLC: $R_f$=0.46 (DCM:MeOH (9:0.5; v/v)); $C_{23}H_{22}F_3N_3O_4$ (461.44), Monoisotopic mass: 461.16. UPLC (purity: >99.9%): $t_R$=7.18 min, (M+H)$^+$462.1. $^1$H NMR (500 MHz, CDCl$_3$) δ 2.60-2.78 (m, 5H), 2.98-3.16 (m, 2H), 3.23-3.38 (m, 3H), 3.63-3.72 (m, 1H), 3.98 (ddd, J=12.89, 6.01, 2.86 Hz, 1H), 6.11 (s, 1H), 6.61 (s, 1H), 6.69-6.73 (m, 2H), 7.21 (t, J=8.0 Hz, 1H), 7.32-7.38 (m, 3H), 7.42-7.44 (m, 2H). $^{13}$C NMR (126 MHz, CDCl$_3$) δ 28.1, 42.3, 45.6, 48.4, 48.6, 56.9, 108.9, 112.2, 114.3, 120.5 (q, J=256.7 Hz), 129.4 (d, J=143.7 Hz), 129.6 (d, J=151.5 Hz), 132.9, 150.3, 152.0, 165.2, 176.4. Enantiomeric purity>99% ($t_R$=35.08 min).

Example 49. (R)-1-(2-Oxo-1-phenyl-2-(4-(3-(trifluoromethyl(sulfanyl)phenyl)piperazin-1-yl)ethyl) pyrrolidine-2,5-dione ((R)-12)

The compound was prepared according to procedure described in Example 44. (R)-4-oxo-4-((2-oxo-1-phenyl-2-(4-(3-((trifluoromethyl)thio)phenyl)piperazin-1-yl)ethyl)amino)butanoic acid (0.99 g, 2.0 mmol, 1 eq) was used as the starting material for the cyclization reaction. The crude product was purified by column chromatography using DCM:MeOH (9:0.5; v/v) eluent system.

White solid. Yield: 86% (0.82 g); m.p. 155.1-155.8° C.; TLC: $R_f$=0.48 (DCM:MeOH (9:0.5; v/v)); $C_{23}H_{22}F_3N_3O_3S$ (477.50), Monoisotopic mass: 477.13. UPLC (purity: >99.9%): $t_R$=7.54 min, (M+H)$^+$478.1. $^1$H NMR (500 MHz, CDCl$_3$) δ 2.68-2.75 (m, 5H), 2.96-3.19 (m, 2H), 3.22-3.43 (m, 3H), 3.62-3.76 (m, 1H), 3.99 (ddd, J=13.17, 5.73, 2.8 Hz, 1H), 6.11 (s, 1H), 6.91 (dd, J=8.3, 2.6 Hz, 1H), 7.06 (s, 1H), 7.12 (d, J=8.0 Hz, 1H), 7.24-7.28 (m, 1H), 7.33-7.38 (m, 3H), 7.42-7.44 (m, 2H). $^{13}$C NMR (126 MHz, CDCl$_3$) δ 28.1, 42.3, 45.6, 48.4, 48.7, 56.9, 123.7, 125.3, 129.6 (q, J=307, 8 Hz), 127.8, 129.4 (d, J=142.4 Hz), 129.1, 130.1, 132.9, 151.4, 165.2, 176.4. Enantiomeric purity>99% ($t_R$=34.82 min).

Example 50. Special Properties of Enantiomers

The effect of the stereochemistry of the compounds according to invention on their anticonvulsant activity was investigated. The anticonvulsant properties were assessed in line with methods described above and results are summarized in Table 3 and Table 4.

TABLE 3

Data from screening studies at a dose of 100 mg/kg for selected enantiomers of compounds according to the general formula (II).

| Compound | Test* | | | |
|---|---|---|---|---|
| | MES | 6 Hz (32 mA) | 6 Hz (44 mA) | scPTZ |
| (R)-3 | 4/4 | 4/4 | — | 3/4 |
| (R)-4 | 4/4 | 4/4 | — | 2/4 |
| (R)-6 | 4/4 | 4/4 | 3/4 | 3/4 |
| (S)-6 | 3/4 | 2/4 | 1/4 | 3/4 |
| (R)-10 | 4/4 | 4/4 | — | 2/4 |
| (R)-12 | 4/4 | 4/4 | — | 1/4 |

*Tests carried out in mice after intraperitoneal administration at a time point of 0.5 h, data indicate the number of mice protected in a given seizure model/number of mice tested; MES-the maximal electroshock test, the 6 Hz (32 mA) and 6 Hz (44 mA) test-the psychomotor seizures induced by low-frequency current (6 Hz) and intensity of 32 mA or 44 mA, respectively;
scPTZ-the subcutaneous seizure test;
"—"-substance not tested.

TABLE 4

The ED$_{50}$ and TD$_{50}$ values for selected enantiomers of compounds according to the general formula (II) and the model AED - valproic acid (VPA) after intraperitoneal administration to mice.

| Compound | ED$_{50}$ [mg/kg] | | | | TD$_{50}$ (mg/kg) | PI (TD$_{50}$/ED$_{50}$) |
|---|---|---|---|---|---|---|
| | MES | 6 Hz (32 mA) | 6 Hz (44 mA) | scPTZ | | |
| (R)-3 | 57.7 | 49.3 | — | 78.3 | 223.0 | 3.7 (MES) |
| | | | | | | 4.5 (6 Hz, 32 mA) |
| | | | | | | 2.8 (scPTZ) |
| (R)-6 | 36.0 | 39.1 | 115.0 | 54.8 | 468.5 | 13.1 (MES) |
| | | | | | | 12.0 (6 Hz, 32 mA) |

TABLE 4-continued

The ED$_{50}$ and TD$_{50}$ values for selected enantiomers of compounds according to the general formula (II) and the model AED - valproic acid (VPA) after intraperitoneal administration to mice.

| Compound | MES | ED$_{50}$ [mg/kg] 6 Hz (32 mA) | 6 Hz (44 mA) | scPTZ | TD$_{50}$ (mg/kg) | PI (TD$_{50}$/ED$_{50}$) |
|---|---|---|---|---|---|---|
| (S)-6 | 68.5 | >130 | — | 75.4 | >300 | 4.1 (6 Hz, 44 mA)<br>8.5 (scPTZ)<br>>4.4 (MES)<br>>4.0 (scPTZ) |
| (R)-10 | 22.6 | 12.8 | — | <60.0 | >150 | >6.6 (MES)<br>11.7 (6 Hz, 32 mA)<br><2.5 (scPTZ) |
| VPA$^g$ | 252.7 | 130.6 | 183.1 | 239.4 | 430.7 | 1.7 (MES)<br>3.3 (6 Hz, 32 mA)<br>2.3 (6 Hz, 44 mA)<br>1.8 (scPTZ) |

The substances were tested 0.5 h after intraperitoneal administration;
MES—the maximal electroshock test, the 6 Hz (32 mA) and 6 Hz (44 mA) test - the psychomotor seizures induced by low-frequency current (6 Hz) and intensity of 32 mA or 44 mA, respectively;
scPTZ—the subcutaneous seizure test;
TD$_{50}$ values were obtained in the rotarod test;
PI—protective index (TD$_{50}$/ED$_{50}$);
"—"—substance not tested.

On the basis of results obtained, it was unexpectedly found that the R-enantiomers exhibit higher biological activity with the desired profile compared to 5-enantiomers.

In particular, in the case of R enantiomers, it was found:
weaker acute neurotoxicity in the rotarod test (see TD$_{50}$ values in Table 2 and Table 4, respectively) in relation to the racemate,
it was also unexpectedly found that the anticonvulsant effect was stereospecific. Enantiomers with the R configuration are characterized by stronger biological activity.

Metabolic stability. The metabolic stability of (R)-6 was assessed according to the methodology described above. Based on the data obtained, an extremely low value of the internal clearance of the compound (R)-6 after incubation with HLMs was found, amounting to CL$_{int}$=2.4 mL/min/kg, indicating its predicted high stability in the human body. In addition, surprisingly and preferably the value of the determined clearance was lower than the value determined for the racemate, compound 6 (CL$_{int}$=5.6), which indicates a lower susceptibility of the enantiomer to metabolic changes. In addition, the results of UPLC analysis revealed that the (R)-6 enantiomer is preferably metabolized to two metabolites—M1 metabolite formed by the dehydrogenation of the piperazine ring, and the M2 metabolite formed by hydroxylation of the phenyl substituent linked to piperazine (FIG. 13). In the case of the racemate, an additional M3 metabolite was observed, most likely obtained by hydroxylation of the side phenyl moiety and reduction of the keto group to hydroxyl in the imide ring (FIG. 7).

Example 51. Preparation of Water-Soluble Salts of Compounds According to the Invention The water-soluble salts of compound according to formula (I) of the invention can be obtained applying the six-step procedure using commercially available tert-butoxycarbonyl (Boc) amino acid derivatives as starting materials. Water-soluble salts were obtained for selected compounds described by formula (I) for which k=0, D is a substituent selected from the group comprising of: H, amino group (—NH$_2$), amino group substituted with one or two aliphatic substituents (in particular —CH$_3$ and/or —C$_2$H$_5$) or an amino group that is part of a heterocyclic ring, where A and B have the meaning as in the case of compound described by formula (II).

A general scheme for the synthesis of water-soluble salts of the compounds described by formula (I) according to invention is shown in FIG. 14. In case the preparation of compounds of formula (I), where D is hydrogen, the procedure described for compounds of formula (II) according to FIG. 2B is used, after which the obtained compound is converted into a water-soluble salt (preferably a hydrochloride) using methods described in the literature.

Steps i and ii are analogous to the procedure described for the synthesis of enantiomers. The amine derivative (VI) undergoes condensation reaction with maleic anhydride, to give the compound with the unsaturated amido-acid structure (VIII). Next, compound VIII is cyclized to compound IX. In the next step, compound of formula IX is subjected to the addition reaction with the appropriate primary or secondary amine. Then the desired compound according to formula (I) is converted into a water-soluble salt (preferably a hydrochloride) using methods described in the literature.

Examples of synthesis as well as physicochemical and spectral data for selected intermediates (VIII, IX) and final products according to FIG. 14 are described below.

Example 52. 4-Oxo-4-((2-oxo-1-phenyl-2-(4-(3-(trifluoromethyl)phenyl)piperazin-1-yl)ethyl) amino) but-2-enoic acid (VIII)

Maleic anhydride (0.98 g 10.0 mmol, 1 eq) was added to a solution of 2-amino-2-phenyl-1-(4-(3-(trifluoromethyl) phenyl)piperazin-1-yl)ethan-1-one (4.61 g 10.0 mmol, 1 eq) in AcOEt (50 mL) and stirred for 30 minutes. After this time, the solvent was distilled off to dryness. The compound was obtained as solid after washing with Et$_2$O.

White solid. Yield: 85% (3.76 g); C$_{23}$H$_{22}$F$_3$N$_3$O$_4$ (461.44), Monoisotopic mass: 461.16. UPLC (purity=96%): t$_R$=6.94 min. (M+H)$^+$462.2.

Example 53. 1-(2-Oxo-1-phenyl-2-(4-(3-(trifluoromethyl)phenyl)piperazin-1-yl)ethyl)-1H-pyrrole-2,5-dione (IX)

ZnCl$_2$ (1.36 g, 10.0 mmol, 1 eq) was added to the suspension of 4-oxo-4-((2-oxo-1-phenyl-2-(4-(3-(trifluoromethyl)phenyl)piperazin-1-yl)ethyl)amino)but-2-enoic acid (4.40 g, 10.0 mmol, 1 eq) in dry benzene (100 mL) and the mixture was heated to 80° C. Then solution of HMDS (2.42 g, 3.14 mL, 15.0 mmol, 1.5 eq) in dry benzene (10 mL) was added dropwise over 30 minutes. The reaction was continued with stirring in reflux for about 24 hours, then cooled and concentrated under reduced pressure. After distilling off the solvent, the oily residue was dissolved in DCM and extracted with 0.1 M HCl (3×50 mL), water (3×50 mL) and saturated NaCl solution (3×50 mL). The organic layer was dried over anhydrous Na$_2$SO$_4$ and then evaporated to dryness. The crude product was purified by column chromatography with DCM:MeOH (9:0.3; v/v) mixture as eluent system. The compound was obtained as solid after washing with Et$_2$O.

White solid. Yield: 79% (3.34 g); C$_{23}$H$_{22}$F$_3$N$_3$O$_4$ (443.43), Monoisotopic mass: 443.15. UPLC (purity=99%): $t_R$=7.45 min. (M+H)$^+$ 444.1.

Example 54. 3-(Methylamino)-1-(2-oxo-1-phenyl-2-(4-(3-(trifluoromethyl)phenyl)piperazin-1-yl)ethyl) pyrrolidine-2,5-dione hydrochloride 2M methylamine solution in THF (0.07 g, 2.2 mmol, 1 eq) was added to a solution of 1-(2-oxo-1-phenyl-2-(4-(3-(trifluoromethyl)phenyl)piperazin-1-yl)ethyl)-1H-pyrrole-2,5-dione (0.98 g, 2.2 mmol, 1 eq) in dry benzene (50 mL). The crude product was purified by column chromatography using DCM:MeOH (9:0.5; v/v) eluent system. The compound was then converted into the hydrochloride salt by treating the compound with a 2M methanolic hydrochloric acid solution.

White solid. Yield: 87% (0.91 g); m.p. 161.2-163.4° C.; C$_{24}$H$_{25}$F$_3$N$_4$O$_3$ (474.48), Monoisotopic mass: 474.19. UPLC (purity: >99.9%): $t_R$=5.53 min, (M+H)$^+$ 475.3. $^1$H NMR (500 MHz, CDCl$_3$) δ 2.76 (br s, 3H), 2.90 (br s, 1H), 3.22 (br s, 2H), 3.38-3.54 (m, 4H), 3.55-3.66 (m, 1H), 3.70 (br s, 1H), 3.84-4.23 (m, 2H), 4.53 (br s, 1H), 6.20 (br s, 1H), 7.18-7.24 (m, 3H), 7.29-7.51 (m, 5H), 7.71 (br s, 1H), 9.98 (br s, 1H).

Example 55. 3-(Dimethylamino)-1-(2-oxo-1-phenyl-2-(4-(3-(trifluoromethyl)phenyl)-piperazin-1-yl) ethyl)pyrrolidine-2,5-dione hydrochloride The compound was prepared according to procedure described in Example 54. 1-(2-oxo-1-phenyl-2-(4-(3-(trifluoromethyl)phenyl)piperazin-1-yl)ethyl)-1H-pyrrolo-2,5-dione (0.98 g, 2.2 mmol, 1 eq) and dimethylamine (0.10 g, 2.2 mmol, 1 eq) were used as starting materials. The crude product was purified by column chromatography using DCM:MeOH (9:0.5; v/v) eluent system. The compound was converted into the hydrochloride salt by treating the compound with a 2M methanolic hydrochloric acid solution.

White solid. Yield: 83% (0.90 g); m.p. 157.8-159.2° C.; C$_{25}$H$_{27}$F$_3$N$_4$O$_3$ (488.51), Monoisotopic mass: 488.20. UPLC (purity: >99.9%): $t_R$=5.53 min, (M+H)$^+$489.3. $^1$H NMR (500 MHz, CDCl$_3$) δ 2.76 (d, J=8.6 Hz, 1H), 2.93 (br s, 2H), 3.06-3.18 (m, 5H), 3.25-3.33 (m, 3H), 3.36-3.41 (m, 2H), 3.41-3.45 (m, 2H), 3.71 (br s, 1H), 3.94-3.98 (m, 1H), 6.14 (s, 1H), 7.01 (d, J=7.4 Hz, 1H), 7.04 (br s, 1H), 7.12 (d, J=7.4 Hz, 1H), 7.34 (t, J=7.7 Hz, 1H), 7.39 (s, 5H), 13.02 (br s, 1H). $^{13}$C NMR (126 MHz, CDCl$_3$) δ 31.4, 42.5 45.7, 48.7, 48.9, 57.7, 60.1, 65.9, 113.1, 117.5, 119, 3, 119.9, 119.7, 124.1 (d, J=272.2 Hz) 129.1, 129.8, 129.9, 131.1, 131.7 (d, J=32.0 Hz) 150.5, 164.4, 169.8, 171.7.

Example 56. 3-(Diethylamino)-1-(2-oxo-1-phenyl-2-(4-(3-(trifluoromethyl)phenyl)piperazin-1-yl)ethyl) pyrrolidine-2,5-dione hydrochloride The compound was prepared according to procedure described in Example 54. 1-(2-Oxo-1-phenyl-2-(4-(3-(trifluoromethyl)phenyl)piperazin-1-yl)ethyl)-1H-pyrrolo-2,5-dione (0.98 g, 2.2 mmol, 1 eq) and diethylamine (0.16 g, 2.2 mmol, 1 eq) were used as starting materials. The crude product was purified by column chromatography using DCM:MeOH (9:0.5; v/v) eluent system. The compound was converted into the hydrochloride salt by treating the compound with a 2M methanolic hydrochloric acid solution.

White solid. Yield: 88% (1.00 g); m.p. 142.2-143.1° C.; TLC: R$_f$=0.52 (DCM:MeOH (9:0.5; v/v)); C$_{27}$H$_{31}$F$_3$N$_4$O$_3$ (516.57), Monoisotopic mass: 516.23. UPLC (purity: >99.9%): $t_R$=5.79 min, (M+H)$^+$ 517.2. $^1$H NMR (500 MHz, DMSO-d$_6$) δ 1.17-1.27 (m, 6H), 2.79-2.89 (m, 1H), 3.05-3.36 (m, 9H), 3.54-3.78 (m, 3H), 4.79 (dd, J=9.2, 5.7 Hz, 1H), 4.92 (dd, J=9.2, 5.7 Hz, 1H), 6.20 (s, 1H), 7.04 (d, J=7.4 Hz, 1H), 7.10 (s, 2H), 7.14 (d, J=8.0 Hz, 1H), 7.31-7.37 (m, 5H), 12.88 (br s, 1H).

Example 57. Special Properties of the Water-Soluble Salts of Compounds According to the Invention The effect of improved water solubility (i.e. salts) of compounds according to the invention on their anticonvulsant activity was investigated. The anticonvulsant properties were assessed in line with methods described above and results are summarized in Table 3 and Table 4.

TABLE 5

Data from screening studies at a dose of 100 mg/kg for selected water-soluble salts according to the general formula (I).

| | Test* | | | |
|---|---|---|---|---|
| Compound | MES | 6 Hz (32 mA) | 6 Hz (44 mA) | ScPTZ |
| 48 | 4/4 | 4/4 | — | 3/4 |
| 49 | 4/4 | 4/4 | — | 3/4 |
| 50 | 4/4 | 4/4 | — | 2/4 |

*Tests carried out in mice after intraperitoneal administration at a time point of 0.5 h, data indicate the number of mice protected in a given seizure model/number of mice tested;

MES-the maximal electroshock test, the 6 Hz (32 mA) and 6 Hz (44 mA) test-the psychomotor seizures induced by low-frequency current (6 Hz) and intensity of 32 mA or 44 mA, respectively;

scPTZ-the subcutaneous seizure test;

"—"-substance not tested.

TABLE 6

The $ED_{50}$ and $TD_{50}$ values for selected water-soluble salt of compounds according to the general formula (I) and the model AED - valproic acid (VPA) after intraperitoneal administration to mice.

| Compound | $ED_{50}$ [mg/kg] | | | | $TD_{50}$ $(mg/kg)^b$ | PI ($TD_{50}/ED_{50}$) |
| --- | --- | --- | --- | --- | --- | --- |
| | MES | 6 Hz (32 mA) | 6 Hz (44 mA) | scPTZ | | |
| 23 | 77.5 | 80.4 | — | <100 | 246.6 | 3.2 (MES) |
| | | | | | | 3.0 (6 Hz, 32 mA) |
| | | | | | | >2.5 (scPTZ) |
| VPA | 252.7 | 130.6 | 183.1 | 239.4 | 430.7 | 1.7 (MES) |
| | | | | | | 3.3 (6 Hz, 32 mA) |
| | | | | | | 2.3 (6 Hz, 44 mA) |
| | | | | | | 1.8 (scPTZ) |

The substances were tested 0.5 h after intraperitoneal administration;
MES—the maximal electroshock test, the 6 Hz (32 mA) and 6 Hz (44 mA) test - the psychomotor seizures induced by low-frequency current (6 Hz) and intensity of 32 mA or 44 mA, respectively;
scPTZ—the subcutaneous seizure test;
$TD_{50}$ values were obtained in the rotarod test;
PI—protective index ($TD_{50}/ED_{50}$);
"—"—substance not tested.

Based on the results obtained, it was found that the salts of the compounds according to the invention show distinctly improved water solubility. This positively affects their pharmacokinetics or/and pharmaceutical properties, and is particularly advantageous in case of intravenous administration of compounds according to the invention.

The invention claimed is:

1. A compound of formula (I) or pharmaceutically acceptable salts thereof,

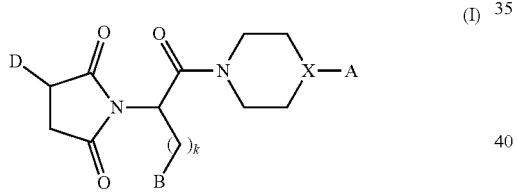

(I)

wherein:
X is N or C,
k is a number equal to 0 or 1,
A is a substituent selected from the group consisting of:
  phenyl substituent;
  a phenyl substituent substituted with one or two or three or four side substituents selected from the group consisting of: halogen atoms, —$SCF_3$, —$CF_3$, —$CHF_2$, —CN, —$OCF_3$, —$NO_2$, —$OCH_3$, —$OC_2H_5$, and alkyl moiety with the number of carbon atoms in the carbon backbone from 1 to 4 with straight or branched chain;
  a phenyl substituent substituted with at least one aromatic or heteroaromatic substituent;
  a benzhydryl substituent;
  a 1-naphthyl or 2-naphthyl substituent;
  a benzothiophenyl substituent selected from the group consisting of: 2-benzothiophenyl, 3-benzothiophenyl, 4-benzothiophenyl, and 5-benzothiophenyl substituents;
  a benzisoxazole substituent selected from the group consisting of: 3-benzisoxazole, 4-benzisoxazole, 5-benzisoxazole, 6-benzisoxazole, and 7-benzisoxazole substituents; and
  an alkyl moiety with the number of carbon atoms in the carbon backbone from 1 to 4, wherein the alkyl moiety has a straight or branched or cyclic chain, wherein the alkyl moiety is optionally substituted with at least one halogen atom;
B is:
  phenyl substituent;
  a phenyl substituent substituted with one or two side substituents selected from the group consisting of: halogen atoms, —$SCF_3$, —$CF_3$, —$CHF_2$, —CN, —$OCF_3$, —$NO_2$, —$OCH_3$, —$OC_2H_5$, and alkyl moiety with the number of carbon atoms in the carbon backbone from 1 to 4 with straight or branched chain;
D is a substituent selected from the group consisting of: H, amino (—$NH_2$), amino group substituted with one or two aliphatic substituents, and an amino group which is part of a heterocyclic ring.

2. The compound according to claim 1, wherein the compound is a compound of formula (II) or a pharmaceutically acceptable salt thereof

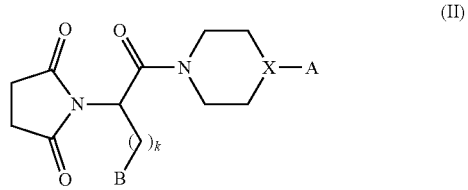

(II)

wherein:
X is N or C,
k is a number equal to 0 or 1,
A is a substituent selected from the group consisting of:
  phenyl substituent;
  a phenyl substituent substituted with one or two or three or four side substituents selected from the group consisting of: halogen atoms, —$SCF_3$, —$CF_3$, —$CHF_2$, —CN, —$OCF_3$, —$NO_2$, —$OCH_3$, —$OC_2H_5$, and alkyl moiety with the number of carbon atoms in the carbon backbone from 1 to 4 with straight or branched chain;

a phenyl substituent substituted with at least one aromatic or heteroaromatic substituent;

a benzhydryl substituent;

a 1-naphthyl or 2-naphthyl substituent;

a benzothiophenyl substituent selected from the group consisting of: 2-benzothiophenyl, 3-benzothiophenyl, 4-benzothiophenyl, and 5-benzothiophenyl substituents;

a benzisoxazole substituent selected from the group consisting of: 3-benzisoxazole, 4-benzisoxazole, 5-benzisoxazole, 6-benzisoxazole, and 7-benzisoxazole substituents; and an alkyl moiety with the number of carbon atoms in the carbon backbone from 1 to 4, wherein the alkyl moiety has a straight or branched or cyclic chain, wherein the alkyl moiety is optionally substituted with at least one halogen atom;

B is:

phenyl substituent;

a phenyl substituent substituted with one or two side substituents selected from the group consisting of: halogen atoms, —SCF$_3$, —CF$_3$, —CHF$_2$, —CN, —OCF$_3$, —NO$_2$, —OCH$_3$, —OC$_2$H$_5$, and alkyl moiety with the number of carbon atoms in the carbon backbone from 1 to 4 with straight or branched chain.

3. The compound according to claim 1, wherein the phenyl substituent substituted with one or two or three or four side substituents selected from the group consisting of: fluorine, chlorine, —SCF$_3$, —CF$_3$, —CHF$_2$, —CN, —OCF$_3$, —NO$_2$, —OCH$_3$, —OC$_2$H$_5$, and alkyl moiety with the number of carbon atoms in the carbon backbone from 1 to 4 with straight or branched chain.

4. The compound according to claim 1, wherein the alkyl moiety with the number of carbon atoms in the carbon backbone from 1 to 4 is substituted with at least one fluorine, at least one chlorine, or both.

5. The compound according to claim 1, wherein k=0.

6. The compound according to claim 1, wherein X is nitrogen.

7. The compound according to claim 1, wherein the substituent A is selected from the group consisting of: 5-benzothiophenyl, 2-naphthyl, and 5-benzisoxazolyl substituents.

8. The compound according to claim 1, wherein the substituent A is (a) phenyl or (b) phenyl substituted with at least one chlorine atom, —CF$_3$, —CHF$_2$, —OCF$_3$, —CH$_3$, —SCF$_3$, or phenyl.

9. The compound according to claim 1, wherein the substituent B is selected from the group consisting of phenyl and phenyl substituted with one or two halogen atoms.

10. The compound according to claim 1, wherein the compound is selected from the group consisting of:

1-(2-Oxo-1-phenyl-2-(4-phenylpiperazin-1-yl)ethyl) pyrrolidine-2,5-dione;

1-(2-(4-(3-Chlorophenyl)piperazin-1-yl)-2-oxo-1-phenylethyl)pyrrolidine-2,5-dione;

1-(2-(4-(3,5-Dichlorophenyl)piperazin-1-yl)-2-oxo-1-phenylethyl)pyrrolidine-2,5-dione;

1-(2-Oxo-1-phenyl-2-(4-(m-tolyl)piperazin-1-yl) ethyl) pyrrolidine-2,5-dione;

1-(2-Oxo-1-phenyl-2-(4-(3-(trifluoromethyl)phenyl)piperazin-1-yl)ethyl)pyrrolidine-2,5-dione;

1-(2-Oxo-1-phenyl-2-(4-(4-(trifluoromethyl)phenyl)piperazin-1-yl)ethyl)pyrrolidine-2,5-dione;

1-(2-(4-(3,5-Bis(trifluoromethyl) phenyl) piperazin-1-yl)-2-oxo-1-phenylethyl) pyrrolidine-2,5-dione;

1-(2-Oxo-1-phenyl-2-(4-(3-(difluoromethyl)phenyl)piperazin-1-yl)ethyl)pyrrolidine-2,5-dione;

1-(2-Oxo-1-phenyl-2-(4-(3-(trifluoromethoxy) phenyl) piperazin-1-yl)ethyl)pyrrolidine-2,5-dione;

1-(2-Oxo-1-phenyl-2-(4-(4-(trifluoromethoxy)phenyl) piperazin-1-yl)ethyl)pyrrolidine-2,5-dione;

1-(2-Oxo-1-phenyl-2-(4-(3-(trifluoromethyl(sulfanyl) phenyl) piperazin-1-yl)ethyl)pyrrolidine-2,5-dione;

1-(2-(4-([1,1'-Biphenyl]-3-yl)piperazin-1-yl)-2-oxo-1-phenylethyl)pyrrolidine-2,5-dione;

1-(1-(4-Fluorophenyl)-2-oxo-2-(4-(3-(trifluoromethyl) phenyl)piperazin-1-yl)ethyl)pyrrolidine-2,5-dione;

1-(2-(4-(Naphth-2-yl) piperazin-1-yl)-2-oxo-1-phenylethyl)pyrrolidine-2,5-dione;

1-(2-(4-(Benzo[b]thiophen-5-yl)piperazin-1-yl)-2-oxo-1-phenylethyl)pyrrolidine-2,5-dione;

1-(2-(4-(1,2-Benzoxazol-5-il)piperazin-1-yl)-2-oxo-1-phenylethyl)pyrrolidine-2,5-dione;

1-(2-(4-(3-Chlorophenyl)piperidin-1-yl)-2-oxo-1-phenylethyl)pyrrolidine-2,5-dione;

1-(2-Oxo-1-phenyl-2-(4-(3-(trifluoromethyl)phenyl)piperidin-1-yl)ethyl)pyrrolidine-2,5-dione; and 1-(2-Oxo-1-phenyl-2-(4-(3-(trifluoromethoxy) phenyl) piperidin-1-yl)ethyl)pyrrolidine-2,5-dione.

11. The compound according to claim 1, wherein the compound is an (R) enantiomer.

12. The compound according to claim 1, wherein the compound is a water-soluble salt.

13. A method for treating epileptic seizures, neuropathic pain or migraine comprising administering the compound in claim 1 to an animal.

14. The compound according to claim 1, wherein D is a substituent selected from the group consisting of: H, amino (—NH$_2$), amino group substituted with one or two of —CH$_3$ and/or —C$_2$H$_5$), and an amino group which is part of a heterocyclic ring.

15. The compound according to claim 1, wherein the alkyl moiety with the number of carbon atoms in the carbon backbone from 1 to 4 is selected from the group consisting of: methyl, ethyl, propyl, isopropyl, n-butyl, sec-butyl, and tert-butyl.

16. The compound according to claim 1, wherein the compound is selected from the following compounds:

(R)-1-(2-(4-(3-chlorophenyl)piperazin-1-yl)-2-oxo-1-phenylethyl)pyrrolidine-2,5-dione;

(R)-1-(2-(4-(3,5-dichlorophenyl)piperazin-1-yl)-2-oxo-1-phenylethyl)pyrrolidine-2,5-dione;

(R)-1-(2-oxo-1-phenyl-2-(4-(3-(trifluoromethyl)phenyl) piperazin-1-yl)ethyl)pyrrolidine-2,5-dione;

(R)-1-(2-oxo-1-phenyl-2-(4-(3-(trifluoromethoxy)phenyl)piperazin-1-yl)ethyl)pyrrolidine-2,5-dione; and (R)-1-(2-oxo-1-phenyl-2-(4-(3-(trifluoromethyl(sulfanyl) phenyl) piperazin-1-yl)ethyl)pyrrolidine-2,5-dione.

17. The compound according to claim 1, wherein the compound is a hydrochloride salt.

18. The compound according to claim 1, wherein the compound is selected from the following compounds:

3-(Methylamino)-1-(2-oxo-1-phenyl-2-(4-(3-(trifluoromethyl) phenyl)piperazin-1-yl)ethyl)pyrrolidine-2,5-dione hydrochloride;

3-(Dimethylamino)-1-(2-oxo-1-phenyl-2-(4-(3-(trifluoromethyl)phenyl)piperazin-1-yl)ethyl)pyrrolidine-2,5-dione hydrochloride; and 3-(Diethylamino)-1-(2-oxo-1-phenyl-2-(4-(3-(trifloromethyl)phenyl)piperazin-1-yl)ethyl)pyrrolidine-2,5-dione hydrochloride.

19. The method of claim 13, wherein the animal is a mouse.

20. The method of claim 13, wherein the animal is a human.

* * * * *